(12) United States Patent
Bryant, Jr. et al.

(10) Patent No.: US 11,378,564 B2
(45) Date of Patent: Jul. 5, 2022

(54) SYSTEMS AND METHODS FOR INTEGRATED AND COMPREHENSIVE MANAGEMENT OF CANNABIS PRODUCTS

(71) Applicant: VYRIPHARM ENTERPRISES, LLC, Houston, TX (US)

(72) Inventors: Jerry L. Bryant, Jr., Houston, TX (US); Tori M. Strong, Houston, TX (US)

(73) Assignee: Vyripharm Enterprises, LLC, Houston, TX (US)

(*) Notice: Subject to any disclaimer, the term of this patent is extended or adjusted under 35 U.S.C. 154(b) by 575 days.

(21) Appl. No.: 16/291,943

(22) Filed: Mar. 4, 2019

(65) Prior Publication Data

US 2019/0195852 A1 Jun. 27, 2019

Related U.S. Application Data

(63) Continuation-in-part of application No. PCT/US2018/042707, filed on Jul. 18, 2018, and a
(Continued)

(51) Int. Cl.
*G01N 33/00* (2006.01)
*G01N 33/94* (2006.01)
(Continued)

(52) U.S. Cl.
CPC ......... *G01N 33/0098* (2013.01); *G01N 33/15* (2013.01); *G01N 33/948* (2013.01); *G06Q 10/087* (2013.01); *G16H 70/40* (2018.01)

(58) Field of Classification Search
CPC .............. G01N 33/948; G01N 33/0098; G06F 2221/2101; G06F 21/57; G06F 21/645; G06F 16/28
See application file for complete search history.

(56) References Cited

U.S. PATENT DOCUMENTS 7,142,988 B1 11/2006 Johnson
9,656,981 B2 * 5/2017 Spigelman ............ C07C 43/215
(Continued)

FOREIGN PATENT DOCUMENTS

EP  2992880 A1  3/2016
EP  2992882 A1  3/2016
(Continued)

OTHER PUBLICATIONS

Preliminary Report on Patentability; PCT Application No. PCT/US2018/042707; dated Jan. 30, 2020.
(Continued)

*Primary Examiner* — Angelica Ruiz
(74) *Attorney, Agent, or Firm* — Polsinelli PC

(57) ABSTRACT

Embodiments of the disclosure provide a method of managing information related to a *cannabis* product across a distributed validated system. The method includes enabling an authorized user to create a plurality of data containing genetic profile of a seed, plant growth conditions of a crop, and manufacturing information used for production of the *cannabis* product, and measurements of quality and quantity of desired components and undesired components in the *cannabis* product. The method includes associating the plurality of data to a record which is identified by a unique identifier. The method includes storing the record into a memory for access by one or more of a plurality of authorized users using the unique identifier. The method includes analyzing the *cannabis* product to determine the quality and quantity of desired components and undesired components in the *cannabis* product. The method includes determining concentration of cannabinoids in the *cannabis* product.

14 Claims, 6 Drawing Sheets

Related U.S. Application Data continuation-in-part of application No. 15/470,562, filed on Mar. 27, 2017, now Pat. No. 10,222,361, which is a continuation of application No. 14/312,051, filed on Jun. 23, 2014, now Pat. No. 9,632,069.

(60) Provisional application No. 62/533,894, filed on Jul. 18, 2017, provisional application No. 61/939,385, filed on Feb. 13, 2014, provisional application No. 61/936,200, filed on Feb. 5, 2014.

(51) Int. Cl.
*G01N 33/15* (2006.01)
*G16H 70/40* (2018.01)
*G06Q 10/08* (2012.01)

(56) References Cited

U.S. PATENT DOCUMENTS

| | | | |
|---|---|---|---|
| 2009/0105128 | A1 | 4/2009 | Bornhop et al. |
| 2010/0119606 | A1 | 5/2010 | Whittle et al. |
| 2010/0286993 | A1 | 11/2010 | Lovelace |
| 2014/0287068 | A1* | 9/2014 | Lewis ............ A01H 5/12 424/725 |
| 2017/0199168 | A1 | 7/2017 | Jackson, Jr. et al. |
| 2018/0167402 | A1* | 6/2018 | Scheidler ............ G06F 21/554 |
| 2018/0285810 | A1 | 10/2018 | Ramachandran et al. |
| 2018/0308046 | A1 | 10/2018 | Schutt |

FOREIGN PATENT DOCUMENTS

| | | |
|---|---|---|
| WO | 2005/009479 A1 | 2/2005 |
| WO | 2005117997 A1 | 12/2005 |
| WO | 2017196655 A1 | 11/2017 |

OTHER PUBLICATIONS

International Search Report; PCT Application No. PCT/US2018/042707; dated Oct. 1, 2018.
The International Search Report and Written Opinion for related PCT Application No. PCT/US2018/042707 dated Sep. 10, 2018.
Translation of Eurasian Search report of Application No. 201791387/31; dated Jan. 22, 2020.
Eurasian Search report of Application No. 201791387/31; dated Jan. 22, 2020.
Extended European Search Report for application No. 20157540.4-1222; dated Apr. 20, 2020.
Examination Report for European Application No. 20 157 540.4-1222; dated Nov. 26, 2021, 6 pages.
Eurasian Office Action for application No. 202090116, dated Feb. 2, 2022, 7 pages.
Xiangyang Liang et al., "Cyclam complexes and their applications in medicine", Chem. Soc. Rev., 2004, vol. 33, p. 246-266 DOI:10.1039/b313659k (see sections 1, 4, especially 4.3.1 on pp. 259-260).
Extended European Search Report for European Application No. 18835211.6, dated Mar. 19, 2021, 6 pages.
Frau S., et al., "Pyrazole-Type Cannabinoid Ligands Conjugated with Fluoro-Deoxy-Carbohydrates as Potential PET-Imaging Agents: Synthesis and CB1/CB2 Receptor Affinity Evaluation," Journal of Fluorine Chemistry, Elsevier, NL, vol. 152, Mar. 18, 2013, pp. 166-172.

* cited by examiner

SYSTEMS AND METHODS FOR INTEGRATED AND COMPREHENSIVE MANAGEMENT OF CANNABIS PRODUCTS

CROSS-REFERENCE TO RELATED APPLICATIONS

This application is a continuation-in-part application of U.S. patent application Ser. No. 15/470,562, filed on Mar. 27, 2017, titled "Integrated Systems and Methods of Evaluating *Cannabis* and Cannabinoid Products for Public Safety, Quality Control and Quality Assurance Purposes," which is a continuation application of U.S. patent application Ser. No. 14/312,051, filed on Jun. 23, 2014, now issued as U.S. Pat. No. 9,632,069, titled "Integrated Systems and Methods of Evaluating *Cannabis* and Cannabinoid Products for Public Safety, Quality Control and Quality Assurance Purposes," which claims the benefit of and priority to U.S. Provisional Patent Application No. 61/936,200, filed on Feb. 5, 2014, titled "Systems and Methods of Evaluating *Cannabis* Products for Public Safety, Quality Control and Quality Assurance Purposes"; and U.S. Provisional Patent Application No. 61/939,385, filed on Feb. 13, 2014, titled "Systems and Methods of Evaluating *Cannabis* Products for Public Safety, Quality Control and Quality Assurance Purposes," the disclosures of which are each hereby incorporated by reference in their entireties. This application is also a continuation-in-part application under 35 U.S.C. § 111(a) of the PCT application No. PCT/US2018/42707, filed on Jul. 18, 2018, titled "Compositions Containing Cannabinoid Analog Conjugates and Methods of Use," which claims the benefit of and priority to U.S. Provisional Patent Application No. 62/533,894, filed on Jul. 18, 2017, titled "Compositions Containing Cannabinoid Analog Conjugates and Methods of Use," the disclosures of which are each hereby incorporated by reference in their entireties.

TECHNICAL FIELD

Embodiments of the disclosure relate generally to the field of managing information about natural products such as *cannabis* and cannabinoid products for quality control and quality assurance purposes. More specifically, embodiments of the present disclosure facilitate a supplier or a consumer of a *cannabis* and/or cannabinoid product to evaluate the efficacy, potency, quality and origin of such product. Embodiments of the disclosure also relate to a *cannabis* and cannabinoid processing center where samples of such products are analyzed for public safety, quality control, and quality assurance purposes. Embodiments of disclosure also relate to testing and tracking medicinal products, such as *cannabis* and *cannabis* products, for evaluation by healthcare professionals and patients for quality control, quality assurance, and therapeutic efficacy.

BACKGROUND

*Cannabis* and cannabinoid products are legally available for human consumption for several purposes, including, but not limited to, medicinal, research and recreational purposes. Undesired and in some cases toxic chemicals, including pesticides and plant growth regulators, tag along with the *cannabis* products and threaten the health of the consumers. As some *cannabis* products can be inhaled rather than eaten, any toxins carried by the products have a direct route into the lungs and blood stream of the consumer. Some states have regulations for controlling the environment where the *cannabis* plants are grown. Most states where *cannabis* products can be legally obtained, have no means for ensuring that the plants are grown under controlled environments. In addition to natural contamination during growth of the plants, *cannabis* and cannabinoid products are unscrupulously contaminated by using extracts or dried parts of other plants, glass particles, industrial chemicals, sugar or sand, and other micro contaminants. There are no robust integrated systems to ensure that the *cannabis* and cannabinoid products are free of chemical and microbiological contamination, and that the product can be traced as the plant is grown, processed into products, and moved to stores for public consumption. Most consumers do not have access to *cannabis* or cannabinoid products that have been tested for purity by third party validated labs.

Medical cannabinoids and botanical drugs have emerged as a viable means of therapy with growing scientific evidence of therapeutic potential. However, very little work has been done for assuring safe *cannabis* product development and consumption, and evaluating the direct correlation to disease outcomes. Various methods of hybridization of the *cannabis* seed has been employed to exploit the variance in cannabinoid profile produced by the plant. However, *cannabis* product characterization and its connection to disease outcomes have yet to be tracked with precision. Variations in methodology can lead to inconsistency in cannabinoid product formation as well as generating other uncertainties in the progeny that cannot be initially predicted, such as increase in terpene production. Without a comprehensive verification/validation process, distortion in medical prognosis and diagnosis of providing recommendation or prescribing *cannabis* for various disease states can arise. Furthermore, public safety and public trust are the thrusts behind policy and regulation surrounding medical *cannabis*. Current platforms lack a comprehensive approach to management of the various aspects of the industry, such as selection of the *cannabis* seed genetics, managing plant growth conditions, production of products and medicaments with directed safety and therapeutic profiles.

SUMMARY

Applicants recognize the public health and safety risks that exist when *cannabis* or cannabinoid products are not accompanied by adequate information about their sources, manufacturing practices, contents, results of any quality testing and quality assurance procedures. Undesired and in some cases toxic chemicals, including pesticides and plant growth regulators, tag along with *cannabis* and cannabinoid products and threaten the health and safety of the consumers, so additional testing and compliance activities may be needed before public consumption. Embodiments of the disclosure include, for example, a *cannabis* processing center where samples of *cannabis* and cannabinoid products are analyzed for research studies to test and set parameters for third parties, such as government agencies for grant awards, public safety, quality control and quality assurance purposes.

Exemplary embodiments of the present disclosure include a method for evaluating one or more *cannabis* and cannabinoid products for use in a particular industry for research, public use, healthcare, or a combination thereof.

By way of example, an embodiment of the disclosure includes a distributed validated *cannabis* testing system. An embodiment of this system includes one or more processors, an input/output unit adapted to be in communication with the one or more processors, one or more *cannabis* databases in communication with the one or more processors to store and associate a plurality of regulatory guidelines with a plurality of measurements of quality and quantity of desired components and undesired components in a *cannabis* product, one or more electronic interfaces positioned to display an online user report and defining one or more *cannabis* user interfaces; and non-transitory computer-readable medium positioned in communication with the one or more processors and having one or more computer programs stored thereon. The computer program includes a set of instructions that when executed by one or more processors cause the one or more processors to perform operations of generating the *cannabis* user interface to display to a user thereof one or more online *cannabis* user reports, the *cannabis* user interface allowing an input of a plurality of information associated with the user or with the *cannabis* product, determining whether the *cannabis* product meets the regulatory guidelines responsive to receiving the plurality of information associated with the user or with the *cannabis* product and information from the one or more *cannabis* databases, associating the plurality of regulatory guidelines with the plurality of measurements of quality and quantity of desired components and undesired components in a *cannabis* product, and outputting to the one or more *cannabis* user interfaces the one or more online *cannabis* user reports, the *cannabis* user reports including one or more of the plurality of information associated with the user or with the *cannabis* product, and one or more of the plurality of measurements of quality and quantity of desired components and undesired components in a *cannabis* product for research or for public use.

Embodiments of the disclosure advantageously provide, for example, sensors, distributed validated systems, computer-readable program products, and related methods to track *cannabis* and cannabinoid products from seed to consumer. The technology disclosed herein relies upon a blockchain-based transaction platform to access and track multiple transactions among various parties involved in manufacture and production of the *cannabis* products and its subsequent delivery for consumption. Any trusted individual or company can access the blockchain-based transaction platform to verify the information associated with any of the transaction records associated with a particular product.

Embodiments of the disclosure provide a distributed validated system and a method for integrating profiling and characterizing of the *cannabis* seed (genetics/multi-omics), plant/growing process (cultivation), processing/manufacturing, information technology (IT)/software services, products, and medicaments. The embodiments disclosed herein facilitate safe administration to subjects and also provide a means of accessing therapeutic intervention outcomes. Embodiments of the disclosure provide methods of tracking, verifying, and validating a *cannabis* product through a platform with integrated and comprehensive management, i.e. a blockchain system, of that product.

Embodiments of the disclosure provide a method of managing information related to a *cannabis* product across a distributed validated system. The method includes enabling a first authorized user to create a first plurality of data containing genetic profile of a seed used for production of the *cannabis* product. The method includes associating the first plurality of data to a first record which is identified by a first unique identifier. The method includes storing the first record into a memory for access by one or more of a plurality of authorized users using the first unique identifier. The method includes enabling a second authorized user to create a second plurality of data containing plant growth conditions of a crop used for production of the *cannabis* product. The method includes associating the second plurality of data to a second record which is identified by a second unique identifier. The method includes storing the second record into the memory for access by the one or more of the plurality of authorized users using the second unique identifier. The method includes enabling a third authorized user to create a third plurality of data containing manufacturing information for production of the *cannabis* product. The method includes associating the third plurality of data to a third record which is identified by a third unique identifier. The method includes storing the third record into the memory for access by the one or more of the plurality of authorized users using the third unique identifier. The method includes analyzing the *cannabis* product to determine quality and quantity of desired components and undesired components in the *cannabis* product using one or more of: cannabinoid profiling, microbiological testing, analytical testing, food testing, acidified food testing, liquid testing, pathogen testing, quality control testing, and quality assurance testing. The method includes determining concentration of one or more cannabinoids in the *cannabis* product. The method includes enabling a fourth authorized user to create a fourth plurality of data containing measurements of the quality and quantity of desired components and undesired components in the *cannabis* product. The method includes associating the fourth plurality of data to a fourth record which is identified by a fourth unique identifier. The method includes storing the fourth record into the memory for access by the one or more of the plurality of authorized users using the fourth unique identifier.

In some embodiments, each of the first identifier, the second identifier, the third identifier, and the fourth identifier provides access to one or more of: the first plurality of data, the second plurality of data, the third plurality of data, and the fourth plurality of data. In some embodiments, each of the first record, the second record, the third record, and the fourth record includes a timestamp. In some embodiments, each of the storing the first record step, the storing the second record step, the storing the third record step, and the storing the fourth record step is validated by the one or more of the plurality of authorized users. In some embodiments, the first plurality of data further includes one selected from the group consisting of: seed purchase request data, grower data, breeder data, seed purchase data, and combinations thereof. In some embodiments, the second plurality of data includes one selected from the group consisting of: seed planting data, soil data, weather data, water data, moisture data, pressure data, light data, nutrient data, pesticide data, microorganism data, toxicant data, crop growth data, harvesting data, storage data, and combinations thereof. In some embodiments, the third plurality of data includes one selected from the group consisting of: supply data, distribution data, extraction data, purification data, and combinations thereof. In some embodiments, the method further includes the step of comparing measurements of the quality and quantity of desired components and undesired components in the one or more *cannabis* products and the concentration of one or more cannabinoids against appropriate regulations for consumption of the *cannabis* product. The method further includes the step of certifying that the *cannabis* products satisfies or fails the appropriate regulations. In some embodiments, the method further includes the step of enabling a fifth authorized user to create a fifth plurality of data containing dose and dosage of the *cannabis* product provided to a consumer. The method further includes the step of associating the fifth plurality of data to a fifth record which is identified by a fifth unique identifier.

The method further includes the step of storing the fifth record into the memory for access by the one or more of the plurality of authorized users using the fifth unique identifier. In some embodiments, the fifth identifier provides access to one or more of: the first plurality of data, the second plurality of data, the third plurality of data, the fourth plurality of data, and the fifth plurality of data. In some embodiments, the fifth record includes a timestamp. In some embodiments, the fifth plurality of data includes one selected from the group consisting of: physician data, pharmacist data, patient data, consumer data, imaging data, treatment data, treatment outcome data, and combinations thereof.

Embodiments of the disclosure provide a method of managing information related to a *cannabis* product across a distributed validated system. The method includes preparing a sample of the *cannabis* product. The method includes testing the sample to determine one or more parameters of: moisture content, microbe/pathogen/mycotoxin profile, pesticide and toxicant profile, residual solvents, heavy metal content, terpene profile, and cannabinoid profile. The method includes enabling an authorized user to create a plurality of data containing parameters obtained in the testing step. The method includes associating the plurality of data to a record which is identified by a unique identifier. The method includes storing the record into a memory for access by one or more of a plurality of authorized users using the unique identifier. In some embodiments, the method further includes the step of storing the *cannabis* product over a predetermined period.

BRIEF DESCRIPTION OF THE DRAWINGS

So that the manner in which the features and benefits of the disclosure, as well as others which will become apparent, may be understood in more detail, a more particular description of the embodiments of the disclosure may be had by reference to the embodiments thereof which are illustrated in the appended drawings, which form a part of this specification. It is also to be noted, however, that the drawings illustrate only various embodiments of the disclosure and are therefore not to be considered limiting of the disclosure's scope as it may include other effective embodiments as well.

DETAILED DESCRIPTION

Figure 1:
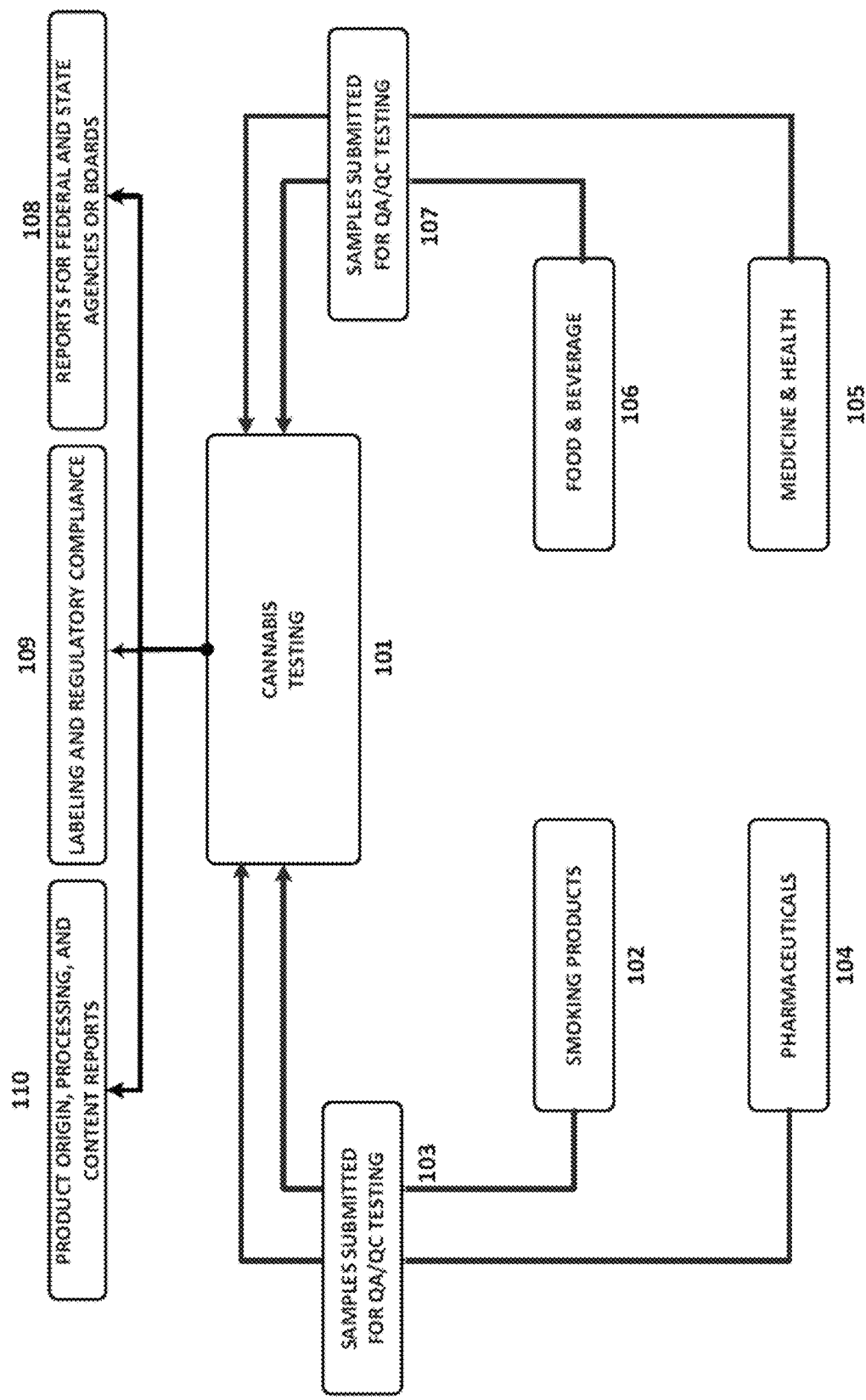
FIG. 1 is a schematic block diagram of an exemplary method according to an embodiment.

The present disclosure will now be described more fully hereinafter with reference to the accompanying drawings, which illustrate various embodiments of the disclosure. This disclosure, however, may be embodied in many different forms and should not be construed as limited to the embodiments set forth herein. Rather, these embodiments are provided so that this disclosure will be thorough and complete, and will fully convey the scope of the disclosure to those skilled in the art. It is to be fully recognized that the different teachings of the various embodiments discussed below may be employed separately or in any suitable combination to produce desired results. The various characteristics mentioned above, as well as other features and characteristics described in more detail below, will be readily apparent to those skilled in the art upon reading the following detailed description of the various embodiments, and by referring to the accompanying drawings. In the drawings and description that follow, like parts are marked throughout the specification and drawings with the same reference numerals, respectively. Certain features of the disclosure may be shown exaggerated in scale or in somewhat schematic form and some details of conventional elements may not be shown in the interest of clarity and conciseness.

The disclosure may use the phrases "in some embodiments," "in various embodiments," "in certain embodiment," or "in embodiments," which may each refer to one or more of the same or different embodiments. Furthermore, the terms "comprising," "including," "having," and the like, as used with respect to embodiments of the present disclosure, are synonymous.

Exemplary embodiments of the present disclosure advantageously provide, for example, sensors, systems, computer-readable program products, and related methods to track *cannabis* and cannabinoid products from seed to consumer. The technology disclosed herein relies upon a blockchain-based transaction platform to access and track multiple transactions among various parties involved in manufacture and production of the *cannabis* products and its subsequent delivery for consumption. Any trusted individual or company can access the blockchain-based transaction platform to verify the information associated with any of the transaction records associated with a particular product.

As used herein, the term "blockchain" refers to a time-dependent growing list of immutable informational objects or records (hereinafter referred to as "blocks") that are linked via cryptography. As used herein, the term "timestamp" refers to a sequence of characters or encoded information identifying when a certain event occurred. The timestamp includes digital date and time information that can be attached to the block. As used herein, the terms "hash" or "hash value" refer to a value resulting from a hash function, which is a function used to map certain data having an arbitrary size to data of a finite size. The hash is a unique identifier associated to a block, and is a key element of the distributed validated system described here. Typically, each block is associated with a timestamp, a hash of the then current block, and a hash associated with the immediately recent block of the then current block.

A seed, as used herein, refers to a unit of reproduction of a plant of the *Cannabis* genus, capable of developing into another such plant. The term is used here to include both a seed that is created by sexual propagation and a cutting or a clone that is an asexual propagation unit. As used herein, a *cannabis* product or a cannabinoid product includes, but is not limited to, any useable product legally intended for research or for human consumption, and containing one or more of Δ-9-tetrahydrocannabinol, 8-tetrahydrocannabinol, cannabichromene, cannabicyclol, cannabidiol, cannabielsoin, cannabigerol, cannabinidiol, cannabinol, cannabitriol, and cannabidiolic acid. *Cannabis* products can include two or more of these cannabinoids in varying proportions. *Cannabis* products can include products that are infused with one or more of the above-identified cannabinoids and are legally intended for human consumption. *Cannabis* products can include products obtained from naturally occurring or genetically modified plants that are scientifically identified as *Cannabis sativa, Cannabis indica*, and *Cannabis rudera-* lis. *Cannabis* products can include products synthesized in a laboratory and containing one or more of Δ-9-tetrahydrocannabinol, 8-tetrahydrocannabinol, cannabichromene, cannabicyclol, cannabidiol, cannabielsoin, cannabigerol, cannabinidiol, cannabinol, cannabitriol, cannabidiolic acid, nabilone, and endocannabinoids like 2-archidonoylglycerol, n-archidonoyldopamine, virodhamine, and noladin ether. A *cannabis* product can include products that are processed to include one or more of the sixty different cannabinoids that have been identified in samples of *cannabis* obtained from naturally occurring or genetically modified plants that are scientifically identified as *Cannabis sativa, Cannabis indica*, and *Cannabis ruderalis*. Embodiments of the disclosure also include the testing of cannabinoid products that are isolated from *cannabis* and documentation of the information as a block. Accordingly, a *cannabis* product as used herein further includes products that include one or more cannabinoids isolated from *cannabis*. *Cannabis* products can come in a variety of forms, including: as a dried plant, resin, in powder form, as oil, as products for smoking, as vaporized products, and also as *cannabis*-infused teas, candies, cookies, and brownies. *Cannabis* products can contain *cannabis* compounds derived from natural sources or otherwise and incorporated along with organic or inorganic components, including, but not limited to, natural, polar, or non-polar solvents. *Cannabis* products can be used for medicinal purposes, research purposes, recreational purposes, or for a combination thereof.

A *cannabis* product or a cannabinoid product includes, but is not limited to, cannabinoid analogs. As used herein, the term "cannabinoid analog" refers to a compound capable of either interacting with cannabinoid receptors in a subject or sharing chemical similarity with cannabinoids or both. Cannabinoid analogs include synthetic or natural cannabinoid compounds that can function as agonists or antagonists. Embodiments of cannabinoid analogs include, but are not limited to, cannabidiol (CBD), cannabidiolic acid (CBDA), cannabidiol monomethylester (CBDM), cannabidiol-C4 (CBD-C4), cannabidivarinic acid (CBDA), cannabidivarin (CBV), cannabidiorcol (CBD-C1), tetrahydrocannabinol (THC), N-arachidonoylethanolamine (AEA) or anandamide, 2-arachidonoylglycerol (2-AG), rimonabant, AM6538, taranabant, otenabant, cannabigerolic acid monomethylether (CBGAM), cannabigerol monomethylether (CBGM), cannabigerovarin (CBGV), cannabigerovarinic acid (CBGVA), cannabichromenic acid (CBCA), cannabichromene (CBC), cannabichromevarinic acid CBCVA), cannabichromevarin (CBCV), Δ-9-tetrahydrocannabinolic acid A (THCA-A), Δ-9-tetrahydrocannabinolic acid B (THCA-B), Δ-9-tetrahydrocannabidiol (THC), Δ-9-tetrahydrocannabinolic acid-C4 (THC-C4), Δ-9-tetrahydrocannabivarinic acid (THCVA), Δ-9-tetrahydrocannabivarin (THCV), Δ-9-tetrahydrocannabiorcolic acid (THCA-C1), Δ-9-tetrahydrocannabiorcol (THC-C1), Δ-7-cis-isotetrahydrocannabivarin (THCV), Δ-8-tetrahydrocannabinolic acid (Δ-8-THCA), Δ-8-tetrahydrocannabidiol (Δ-8-THC), cannabicyclolic acid (CBLA), cannabicyclol (CBL), cannabicyclovarin (CBLV), cannabielsoic acid A (CBEA-A), cannabielsoic acid B (CBEA-A), cannabielsoin (CBEA-A), cannabinolic acid (CBNA), cannabinol (CBN), cannabinol methylether (CBNM), cannabinol-C4 (CBN-C4), cannabinol-C2 (CBN-C2), cannabiorcol (CBN-C1), cannabinodiol (CBND), cannabinodivarin (CBVD), cannabitriol (CBT), 10-ethoxy-9-hydroxy-Δ-6a-tetrahydrocannabinol, 8,9-dihydroxy-Δ-6a-tetrahydrocannabinol, cannabitriolvarin (CBTV), and ethoxy-cannabitriolvarin (CBTVE).

A *cannabis* product or a cannabinoid product includes, but is not limited to, theranostic compositions containing label-chelator-medical cannabinoid analog conjugates. The labels can be radionuclides that are used to label a medical cannabinoid analog through a chelator. Certain embodiments include cyclam (N4) as the chelator. As used herein, the term "theranostic" refers to agents or applications that can function in both diagnostic and therapeutic modalities.

As used herein, the term "chelators" refer to compounds that form coordination complexes upon binding with metal ions or other substrates. The structure of chelating ligands and the metals that are chelated to them may be varied depending on the desired use. Many ligands that bind to radionuclide metals are tetradentate and contain a combination of four nitrogen and/or sulfur metal coordinating atoms (i.e. N4, N3S, N2S2 and the like). Example of chelators that can be used here includes cyclam compounds (N4), diethylentriamine pentaacetic acid (DTPA), tetraazacyclododecane-N,N',N'', N'''-tetraacetic acid (DOTA), ethylenediaminetetraacetic acid (EDTA), dimercaptosuccinic acid (DMSA), sulfur colloid, and $N_2S_2$ systems such as MAMA (monoamidemonoaminedithiols), DADS (N2S2 diaminedithiols), CODADS and the like. These chelator systems and a variety of others are described in Liu and Edwards, *Chem Rev.* 1999, 99 (9), 2235-2268; $N_2S_2$ is also described in U.S. Pat. No. 4,897,225; 5,164,176; or 5,120,526. Method for synthesis of certain N4 compounds is described in U.S. Pat. No. 5,880,281 but they can also be obtained from commercial sources such as Sigma Aldrich Chemical (Milwaukee, Wis.) and TCI America (Portland, Oreg.). Certain N4 compounds which can be used as chelators may include but not limited to, 1,4,7,10-tetraazacyclododecane (Cyclen), 1,4,7,10-tetraazacyclotridecane (Cyclam 13), 1,4,7,11-tetraazacyclotetradecane (Isocyclam), 1,5,9,13-tetraazacyclohexadecane, 1,5,9,13-tetraazacycloheptaadecane, 1,5,9,14-tetraazacyclooctadecane, 1,5,10,14-tetraazacyclooctadecane, 1,5,10,15-tetraazacyclodononadecane, which are described in U.S. Pat. Nos. 8,758,723, 6,093,382; 5,608,110; 5,665,329; 5,688,487, U.S. Pat. Pub. No. 2012/0276005, and PCT/GB2005/002807. Other examples of chelator moieties include but not limited to, tetraazacyclododecane-N,N',N'', N'''-tetra-acetic acid, monoamide (DOTA-MA); 10-(2-hydroxypropyl)-1,4,7,10-tetraazacyclododecane-1,4,7-triacetic acid (HP-DO3A). N4 is conjugated to a medical cannabinoid compound and further chelated to a metal. N4 has a closed-ring structure that helps stabilize the radionuclides. Chelators with higher lipophilicity, such as N4, also confer decreased renal and hepatic toxicity because they have shown decreased accumulation in these organs, resulting from greater uptake by the targeted cells. Conjugation of DOTA to highly selective $CB_2$ receptor inverse agonist SR144528 following by chelation of Gallium (Ga), Technetium (Tc), Copper (Cu) or with lanthanide series such as Gadolinium (Gd), Europium (Er), Terbium (Tb) is described in U.S. Pat. No. 8,367,714. Imaging $CB_1$ receptor using various radiotracers is described in PCT/US2009/043491. Radioligands with high affinity and selectivity for CBi receptors such as 3,4-diarylpyrazoline derivatives were labeled a radioisotope selected from the group consisting of $^2H$, $^{14}C$, $^{13}N$, $^{18}F$, $^{75}Br$, $^{76}Br$, and $^{123}I$ for imaging with PET or SPECT. U.S. Pat. Nos. 8,840,865, 9,617,215, 8,323,621, U.S. Pat. Pub. No. 2005/0070596, and WO2007130361 describe imaging of cannabinoid system for medical and therapeutic purposed to treat for instance inflammatory diseases, cancer, neurological disorders therapeutics and medical imaging.

As used herein, the term "label" refers to an atom, a molecule, or a compound that is used to identify the location of the composition to which the label is attached. Labels can have one or more of fluorescent, phosphorescent, luminescent, electroluminescent, chemiluminescent or other spectroscopic properties. These properties enable the detection and identification of the label-chelator-medical cannabinoid analog conjugates using any technique capable of detecting and identifying the label, including visible light, ultraviolet and infrared spectroscopy, Raman spectroscopy, nuclear magnetic resonance, positron emission tomography, and other methods known in the art.

As used herein, the term "imaging" refers to all tissue visualization processes using electromagnetic wave technologies for which the instant compositions can be used, including but not limited to cells of the nervous system, blood cells, cancerous cells, and precancerous cells. Provided here are kits for imaging neurologic cells. In an embodiment, the kit contains a predetermined quantity of a conjugate of a chelator and a medical cannabinoid analog; and a predetermined quantity of an imaging agent. The conjugate of the chelator and the medical cannabinoid analog can be present in the kit as precursors that subsequently interact with the imaging agent, when provided with suitable reaction conditions. The kit can also include a tin-containing reducing agent. Also provided here are kits for genomic or other omic assays that contain a predetermined quantity of a conjugate of a chelator and a medical cannabinoid analog; and a predetermined quantity of an imaging agent.

As used herein, the terms "radionuclide," "radioactive nuclide," "radioisotope," or "radioactive isotope" are synonymous. One or more different radioisotopes can be used as labels. The non-limiting examples of radionuclides include $^{99m}Tc$, $^{117m}Sn$, $^{177}Lu$, $^{188}Re$, $^{186}Re$, $^{153}Sm$, $^{166}Ho$, $^{90}Y$, $^{89}Sr$, $^{67}Ga$, $^{68}Ga$, $^{111}In$, $^{186}Gd$, $^{59}Fe$, $^{225}Ac$, $^{212}Bi$, $^{211}At$, $^{45}Ti$, $^{60}Cu$, $^{61}Cu$, $^{67}Cu$, $^{64}Cu$ and $^{62}Cu$. In other aspects, the metal ion is a non-radioactive metal such as $^{187}Re$, $^{69}Ga$, and $^{193}Pt$.

A *cannabis* product that is evaluated under embodiments of the disclosure can be received from a variety of sources, including, but not limited to, growers, farmers, producers and processors of the *cannabis* products and wholesale and retail sales entities of the *cannabis* products. As used herein, producers include a person or an entity authorized by a state or federal control board or agency to grow, plant, cultivate, harvest, or be similarly involved in production of naturally occurring or genetically modified plants that are scientifically identified as *Cannabis sativa, Cannabis indica*, and *Cannabis ruderalis*. Producers also include a person or an entity authorized by a state or federal control board or agency to procure raw materials, and chemically manufacture, or be similarly involved in production of *cannabis* products.

As used herein, a processor of a *cannabis* product can include, but is not limited to, a person or an entity authorized by a state or federal control board or agency to process naturally occurring or chemical raw materials to produce *cannabis* products, package and label *cannabis* products for sale in retail outlets, and sell *cannabis* products to wholesale and retail sales entities.

As used herein, a retail sales entity of a *cannabis* product can include, but is not limited to, a person or an entity authorized by a state or federal control board or agency to sell *cannabis* products in a retail outlet. As used herein, a retail outlet can include, but is not limited to, a location authorized by a state or federal control board or agency for the retail sale of *cannabis* products. For example, without limitations, federal agencies such as the US Department of Agriculture, the Food and Drug Administration, and the Drug Enforcement Agency can regulate the consumption of the *cannabis* products and provide the required guidelines for testing the *cannabis* products. For example, without limitations, retail sales entities in the state of Washington include entities that sell *cannabis* products under a license from the Washington Liquor Control Board. For example, without limitations, retail sales entities in the state of Colorado include entities that sell *cannabis* products under a license from the Marijuana Enforcement Division.

As used herein, users can include, but are not limited to, persons or entities who use or benefit from certain embodiments of the disclosure by receiving information regarding the *cannabis* products. Users can also include producers of the plant, manufacturers and distributors of the *cannabis* products, researchers or healthcare professionals at government and private entities, and wholesale and retail sales entities of the *cannabis* products. Users can also include persons or entities who receive through legal means the *cannabis* products from producers of the plant, manufacturers and distributors of the *cannabis* products, and wholesale and retail sales entities of the *cannabis* products. Users can also include, but are not limited to, people who consume the *cannabis* product for medicinal or recreational purposes, or for any legally approved reason. Users can also include, but are not limited to, individuals who are employees or agents of governmental agencies (such as researchers whom may be performing studies for non-human or human use), and have a legal reason to access the information associated with the *cannabis* products. As used herein, the term "subject" refers to all kinds of animals including humans, rodents, other mammals, or avian species. The cannabinoid-based compositions can serve as a diagnostic agent, a prognostic agent, or an agent to alleviate or treat a disease in a subject. The target site can be any tissue of the subject, including but not limited to the brain, heart, lung, esophagus, intestine, breast, uterus, ovary, prostate, testis, stomach, bladder, or liver. Also, embodiments provided herein can be used as agents to target diseases, such as cancer or neurologic, gastrointestinal, metabolic, and neuroendocrine disorders. As used herein, the term "administration" refers to an activity of introducing a composition described herein to a subject by an appropriate method, and the composition may be administered via various routes of intravenous, oral, intramuscular, transdermal, intra-peritoneal, topical, sublingual, buccal, inhalation, nasal, or ophthalmic routes as long as they can deliver the same to the target tissues. The compositions described herein can be delivered as pharmaceutical formulation.

As used herein, users can include, but are not limited to, persons or entities who are involved in the generation and use of specific *cannabis* products for precision medicine. For example, these specific *cannabis* products include theranostic compositions that target the endocannabinoid system (ECS) implicated in the pathogenesis of neurologic disorders and cancer. This individualized medicine platform allows delivery of personalized medicines designed on the basis of individual genetic make-up, biochemistry, molecular imaging, molecular blueprint, and clinical observations and measurements associated to each patient's disease. In another example, these specific *cannabis* products are part of compositions for imaging or treatment of diseased cells. Certain compositions contain a cannabinoid analog and a chemotherapeutic agent. Certain composition contain a chemotherapeutic agent and a cannabinoid analog conjugated to a chelator. In certain embodiments, the chelator is cyclam. In certain embodiments, the cannabinoid analog is a cannabidiol. Certain embodiments include compositions containing a combination of a chemotherapeutic agent and a cannabinoid analog conjugated to a chelator and a label. In certain embodiments, the chemotherapeutic agent is Bruton's tyrosine kinase inhibitors, such as ibrutinib (IBN) and zanubrutinib (BGB). In certain embodiments, the chemotherapeutic agent is a proteasome inhibitor, such as carfilzomib (CFZ). In certain embodiments, the chemotherapeutic agent is tumorex (TMX).

Information regarding the *cannabis* products involve any or some or all information associated with origin, efficacy, potency, quality and quantity of desired components and undesired components in the *cannabis* products, the governmental licenses and authorizations for the *cannabis* products, therapeutic outcomes following administration or consumption of such products, or any combinations of the information thereof. Desired components in *cannabis* products include, without limitations, chemical components and biological components of a *cannabis* product that allow the *cannabis* product to meet the requirements for sale or for human consumptions in a particular industry. Desired components, for example without limitations, include cannabinoids, pharmaceutically acceptable salts, pharmaceutical fillers, taste additives, and food coloring. Undesired components in *cannabis* products can include, without limitations, chemical components and biological components of a *cannabis* product that cause the *cannabis* product unfit for sale in a particular industry. Undesired components, for example without limitations, include pathogenic microorganisms and toxic chemicals like pesticides, fertilizers, and plant growth regulators. Desired components in a *cannabis* product in a particular industry may be undesired components in another industry. As used herein, the term "pharmaceutically acceptable salt" refers to those salts, which retain the biological effectiveness and properties of the parent compound. And unless otherwise indicated, a pharmaceutically acceptable salt includes salts of acidic or basic groups, which may be present in the compounds of the formulae disclosed herein. Certain *cannabis* products include conjugates of a chelator and a targeting ligand. Such products may be used for imaging, diagnostic and/or therapeutic purposes.

In certain embodiments, the *cannabis* product that is tracked through the distributed validated *cannabis* testing system is a pharmaceutical formulation. A "pharmaceutical formulation" refers to a mixture of one or more of the compounds described herein, or a pharmaceutically acceptable derivative as an active ingredient, and at least one pharmaceutically acceptable carrier or excipient. The purpose of a pharmaceutical composition is to facilitate administration of a compound to a subject. In another aspect, a pharmaceutical composition can contain a compound of one of the formulae described herein, or a pharmaceutically acceptable derivative, and a pharmaceutically acceptable carrier or excipient. In some embodiments, the pharmaceutical composition includes two or more pharmaceutically acceptable salts, acids, esters, excipients, carriers, diluents, and combinations thereof. The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the active ingredient. For example, the term "a pharmaceutically acceptable derivative" of compounds described herein includes all derivatives of the compounds described herein (such as salts, pro-drugs, metabolites, esters, ethers, hydrates, polymorphs, solvates, complexes, and adducts) which, upon administration to a subject, are capable of providing (directly or indirectly) the compounds described herein.

For example, the *cannabis* products being tracked through the distributed validated *cannabis* testing system include cannabinoid-based compositions used for imaging diseased cells. These compositions can be applied in the diagnosis, assessment, and treatment of any medical disorder and the information associated with the subjects receiving these compositions is also an input into the distributed validated *cannabis* testing system. The diseases may include various forms of neurologic disorders and cancer. In particular, cancer can include one or more carcinoid, neuroendocrine cancer, breast cancer, lung cancer, prostate cancer, ovarian cancer, brain cancer, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, colorectal cancer, and cancers of hematopoietic origin such as lymphoma, or leukemia. The neurologic diseases can include Alzheimer's disease (AD), Parkinson's disease (PD), Huntington's disease (HD), amyotrophic lateral sclerosis (ALS), multiple sclerosis, posttraumatic stress disorder (PTSD), epilepsy, seizures, Tourette's syndrome, schizophrenia, anxiety disorders, autism, depression, dementia, and other diseases and disorders that implicate the nervous system.

The distributed validated *cannabis* testing system also includes blocks from users of the imaging modalities using these *cannabis* products, and containing information such as sensitivity and specificity, patient administration issues, and adverse effects. Other information can also include the time and costs data associated with any of the foregoing. Health professionals can access blocks of information to track the particular *cannabis* product that has been administered to the subject. The professionals can also input and access information related to the diagnosis, prognosis, and treatment of the patient, especially when that patient is being treated or under treatment with medical cannabinoids. Certain embodiments include methods of imaging at the site of a disease in a given subject to perform a pre- or post-treatment evaluation and to be able to monitor that subject for as long as that subject is being treated or under treatment with medical cannabinoids. In certain embodiments, the diagnostic laboratory systems also provide data to the distributed validated *cannabis* testing system. Accordingly, any imaging modality can be used to detect signals from the one or more labels. Non-limiting examples of imaging methods used to detect the signals from the labels include PET, PET/CT, CT, SPECT, SPECT/CT, MRI, near-infrared (NIR), optical imaging, optoacoustic imaging, and ultrasound.

The distributed validated *cannabis* testing system also includes blocks from manufacturers of kits that contain an imaging probe, a diagnostic agent, or a pharmaceutical composition. Certain specific embodiments include blocks from systems involved in imaging, testing, diagnosing, or delivering a *cannabis*-based composition for the treatment of physiological disorders. Authorized users of the distributed validated *cannabis* testing system can access and provide input regarding the personalized and efficacious dose and dosing regimens involving the use of medical cannabinoids.

The distributed validated *cannabis* testing system also includes blocks from manufacturers, suppliers, and distributors of the cannabinoid-based compositions, such as the label-chelator-medical cannabinoid analog conjugates. These conjugates can include phytocannabinoids that are naturally occurring plant-derived cannabinoids. The manufacturers, suppliers, and distributors of the medical cannabinoids are involved in the manufacturing, extraction, purification, and distribution of these naturally occurring compounds that are isolated from plants. The cannabinoid-based compositions also include label-chelator-terpenoid analog conjugates, label-chelator-flavonoid conjugates, and label-chelator-phytosterol conjugates. Among the natural medical phytocannabinoids, Δ-9-tetrahydrocannabinol (Δ-9-THC), cannabidiol (CBD), and cannabinol (CBN) are the most abundant, yet other phytocannabinoids can play a very important role in precision medicine. Based on structure, binding properties and signaling/function features, medical cannabinoids are grouped into distinct classes: (i) the classical medical cannabinoids, which include both natural plant extracts such as Δ-9-THC and chemically synthesized compounds such as Marinol; (ii) nonclassical medical cannabinoids, mainly exemplified by the synthetic cannabinoid receptor (CB) agonist CP-55,940; (iii) aminoalkylindoles, which include chemically produced cannabinoids like AM1241; (iv) diarylopyrazoles, which include CB inverse agonists (or antagonists) such as SR141716A, also known as rimonabant; and (v) endogenous endocannabinoids, which are naturally produced by animal and human cells and include N-arachidonoylethanolamine, (AEA) or anandamide, 2-arachidonoylglycerol (2-AG), noladin ether, virodhamine and N-arachidonylodopamine (NADA). Examples of the label-chelator-medical cannabinoid analog conjugate include the medical cannabinoids, such as dronabinol, nabilone, nabiximols, cannador, cannabidiol, cannabinol, cannabigerol, tetrahydrocannabivarin, and cannabichromene. Examples of the label-chelator-medical cannabinoid analog conjugate include medical cannabinoids such as HU-210, Δ-9-THC, Δ-8-THC and desacetyl-L-nantradol, which are recognized as CB1/CB2 receptor agonists, without distinctive specificity for either receptor. Δ-9-THC stands out as a *C. sativa* cannabinoid, which exhibits CB1/CB2 affinity and the highest psychotropic effects. By a pentyl substitution on Δ-8-THC side chain, conversion into the HU-210 analog occurs, with increased receptor affinity. Other structural modifications of the THC backbone lead to new and selective CB2 agonists JWH-133, JWH-139, and HU-308 and L-759633 and L-759656, which display affinities at the nanomolar range. Examples of the label-chelator-medical cannabinoid analog conjugate include non-classical medical cannabinoids, which are a family of bicyclic (AC) and tricyclic ACD medical cannabinoids. They are prominently represented by CP55940, along with CP55244 and CP47497 analogs. Of note, CP55940 is the best-known medical cannabinoid agonist, which displays a potent in vivo effect via shared CB1 and CB2 signaling. Examples of the label-chelator-medical cannabinoid analog conjugate include aminoalkylindoles. R-(+)-WIN55212 is the prototype of this family with medical cannabinoid-like features, which can bind both CB1 and CB2 receptors but exhibits higher specificity for CB2 and can mimic in vivo THC-mediated effects. Other analogs like JWH-015 and L-768242 also show similar CB2 affinity as R-(+)-WIN55212. Examples of the label-chelator-medical cannabinoid analog conjugate include medical diarylpyrazoles, which are a class of medical cannabinoid analogs whose distinctive function is to inhibit CB1 or CB2-dependent intracellular signaling pathways, acting as antagonists (inverse agonist); for example, embodiments include SR141716A, AM251 and AM281 that inhibit CB1 receptor mediated effects. Examples of the label-chelator-medical cannabinoid analog conjugate can include certain endocannabinoids. N-arachidonoylethanolamine (AEA), or Anandamide, is an example of an eicosanoid that is converted into its active form, via the omega-3 (ω-3) and omega-6 (ω-6) biosynthetic fatty acid pathways, and specifically targets CB receptors in mammals. Consequently other eicosanoids that can function in these embodiments include methanandamide (R and S isomers), arachidonyl-2-chloroethylamide (ACEA), arachidonylcyclopropylamide (ACPA) and 2-arachidonoylglycerol (2-AG), which exhibit binding affinity to CB1 and CB2.

The distributed validated *cannabis* testing system also includes blocks from systems used by consumers, patients, and healthcare professionals, who utilize medical cannabinoid-based compositions as theranostic agents targeting serious pathologies, such as cardiovascular, neurological, psychiatric, immunological, endocrine and neoplastic disorders. For example, authorized users of the distributed validated *cannabis* testing system can access and input information regarding the impact of the medical cannabinoid-based compositions in health and disease and the early success or failure for specific applications. In a specific example, authorized users of the distributed validated *cannabis* testing system can access and input information regarding the effect of the specific medical cannabinoid analog in the management of chronic pain.

For example, authorized users of the distributed validated *cannabis* testing system can access and input information regarding the ECS and other pathways that modulate parallel functions aimed at protecting and maintaining a subject's homeostasis. CB1 is mainly expressed in central and peripheral nervous system but discrete distribution has been observed in other tissues. Thus, utilization of the label-chelator-medical cannabinoid analog conjugates directed to CB1 signaling can result in broad and pleiotropic actions. Although the CB1 receptor has been known to primarily regulate functions associated to cognition, memory, perception, mood, behavior and psychotropic activities, there is increasing evidence that it can play a role in analgesia, cardiovascular, respiratory, and reproductive functions, as well in the maintenance of overall homeostasis. CB2 receptors are predominantly expressed in immune competent organs where cells undergo antigen-dependent maturation and selection programs, which empowers them to survey and mount powerful responses against pathogens and aberrantly developed cells. CB2 exhibits a relatively limited distribution in the central nervous system (CNS). CB2-dependent activation involves regulatory mechanisms that support immune cell migration to the site of inflammation and the release cytokines. The expression of CB2 is particularly important for CNS microglia, as demonstrated by the capacity of medical cannabinoid agents to reduce cytokine-mediated neuro-inflammation. Embodiments of the label-chelator-medical cannabinoid analog conjugate that include specific CB2 ligands, such as O-3223 (a synthetic CB2 specific agonist), can be used for anti-inflammatory and anti-nociceptive applications, without apparent CB1-like mediated effects.

For example, authorized users of the distributed validated *cannabis* testing system can access and input information regarding the manufacture, distribution, supply, administration and use of compositions containing the label-chelator-terpenoid conjugates and contribute to the blockchain with information about the antioxidant, anti-inflammatory, analgesic, anticancer, antibiotic and anti-psychiatric (anxiety and depression) benefits of terpenoid compounds. For example, authorized users of the distributed validated *cannabis* testing system can access and input information regarding the manufacture, distribution, supply, administration and use of compositions containing the label-chelator-flavonoid conjugates and contribute to the blockchain with information about the antioxidant, anti-inflammatory and anticancer properties of flavonoid compounds, including polyphenol *cannabis* flavonoids. The *cannabis* flavonoids can provide significant cardiovascular protection, particularly improving coronary and peripheral circulation by maintenance of homeostatic blood pressure, prevention of the formation of blood clots, and reduction of atherosclerosis risks. Mechanisms of *cannabis* flavonoids mediated antioxidative and anti-inflammatory effects include apigenin (4',5,7-trihydroxyflavone)-dependent inhibition of TNF-α, which has also shown to exhibit therapeutic benefits in multiple sclerosis and rheumatoid arthritis. For example, authorized users of the distributed validated *cannabis* testing system can access and input information regarding the manufacture, distribution, supply, administration and use of compositions containing the compositions containing the label-chelator-phytosterol conjugates and contribute to the blockchain with information about the cardiovascular protection, anti-inflammation, and anti-systemic edema properties of phytosterol compounds, including medical *cannabis* phytosterols. In another example, authorized users of the distributed validated *cannabis* testing system can access and input information regarding the manufacture, distribution, supply, administration and use of compositions containing synthetic antagonists, such as taranabant, otenabant, and AM6538, as well as the inverse agonist/antagonist rimonabant.

In certain embodiments, a *cannabis* product received from any one or more of the sources described above can be subjected to a variety of testing protocols for research or public use that detect the quality and quantity of desired components and undesired components. A supplier, researcher, healthcare professional, or a consumer of one or more *cannabis* products can evaluate the origin, efficacy, potency, and quality of the one or more *cannabis* products by accessing information obtained from other actors in the supply chain or as obtained through a variety of testing protocols. Quantity of desired components and undesired components in a *cannabis* product can be expressed in terms of absolute weight, absolute volume, or relative weight or relative volume as compared to other components in the *cannabis* product. Testing protocols can include one or more analytical tests and methods of separation, identification, and quantification of the chemical components. For example without limitations, a *cannabis* product can be subjected to a battery of routine analytical tests or to a specialized research study. Testing protocols can include without any limitation, one or more of the following: microbiological testing, analytical testing, food testing, acidified food testing, liquid testing, pathogen testing, quality control, quality assurance, additional testing services, or combinations thereof. Analytical tests, for example without limitations, can include extractables/leachables studies, reference standard characterization, structural elucidation of target/lead compounds, structural elucidation of unknowns, impurity and degradation studies, identification and characterization of the quantity of chemical components, synthesis and purification of impurities and degradation products, and elemental analysis of the *cannabis* products. Analytical tests, for example without limitations, can include tests establishing the cannabinoid profile, and the efficacy and potency of the cannabinoids present, tests determining the dosage delivered by a particular formulation or food product, and tests for producing products with the appropriate dose. The cannabinoid profile includes the identification and quantification of at least the major cannabinoids found within a *cannabis* product. For example, in certain embodiments, determining the quantity of desired components in a *cannabis* product includes determining the concentration of one or more cannabinoids in the one or more *cannabis* products. For example, in certain embodiments, the quantity of desired components like tetrahydrocannabinol (THC) along with other cannabinoids and terpenoids can be determined by either liquid chromatography, mass spectrometry or both. This is especially important for edible forms of *cannabis* products, where a greater percentage of active ingredients reach the bloodstream. Appropriate dosage can bring about medicinal or health benefits to the consumer, while excess or improper dosage can have detrimental side effects.

As used herein, microbiological testing can include but is not limited to testing protocols that detect, for example, the presence of microorganisms, the type of microorganisms, the quantity, or combinations thereof. Examples of microbiological testing include total plate count, aerobic plate count, anaerobic plate count, psychrotrophic plate count, probiotic, genomic, proteomic and multi-omic testing. Examples of undesired microorganisms include, without limitations, *E. coli*, coliforms, lactic acid bacteria, mesophilic spore formers, mold, yeast, and thermophilic spore formers.

As used herein, food testing can include but is not limited to testing protocols for the food industry that detect the quality and quantity of desired components and undesired components, for example without limitations, the presence of microorganisms, the type of microorganisms, the quantity, or combinations thereof. Examples of food testing include total plate count, aerobic plate count, anaerobic plate count, psychrotrophic plate count, probiotic, genomic, proteomic and multi-omic testing. Examples of undesired microorganisms include, without limitations, coliforms, *E. coli, Salmonella, Staphylococcus aureus*, and fungi like yeasts and molds.

As used herein, liquid testing can include but is not limited to testing protocols that test liquids containing *cannabis* products to detect the quality and quantity of desired components and undesired components. For example without limitations, a *cannabis* product in a liquid form can be tested for the presence of microorganisms, the type of microorganisms, the quantity, or combinations thereof. Examples of liquid testing include total plate count, aerobic plate count, anaerobic plate count, probiotic, genomic, proteomic and multi-omic testing. Examples of undesired microorganisms include, without limitations, coliforms including fecal coliforms, *E. coli, Salmonella, Staphylococcus aureus*, and fungi like yeasts and molds. Certain embodiments of the disclosure include testing protocols for detecting the presence and quantity of pathogenic microorganisms, for example, without limitations, *Bacillus cereus, Campylobacter, Chronobacter, Clostridium perfringens,* Hemorrhagic *E. coli* (O157:H7), *Listeria monocytogenes,* Non-O157 STEC *E. coli, Salmonella, Staphylococcus aureus, Shigella, Vibrio,* and *Yersinia*.

In certain embodiments of the disclosure, a *cannabis* product received from any one or more of the sources described above can be subjected to a variety of testing protocols that determine compliance regulatory guidelines from federal and state agencies and boards, including, but not limited to, guidelines for labeling, packaging, compounding, administering to a patient, or marketing, or combinations thereof. For example, without limitations, federal agencies that regulate labeling of food products include the FDA and the USDA. Examples of regulatory guidelines also include, without limitations, guidelines regarding labeling, nutritional claims, monitoring and rating of *cannabis* products, or combinations thereof. Another embodiment of the disclosure, in consultation with one or more federal and state agencies or boards, is a method of establishing appropriate standards for *cannabis* products according to grade, condition, cannabinoid profile, THC concentration, or other qualitative and quantitative measurements deemed acceptable or compliant by the one or more federal and state agencies or boards.

In certain embodiments of the disclosure, a *cannabis* product received from any one or more of the sources described above can be subjected to a variety of testing protocols to determine compliance with *cannabis* product labeling guidelines from federal and state agencies and boards. For example, without limitations, federal agencies that regulate labeling of food products include the FDA and the USDA. Examples of labeling guidelines include, without limitations, guidelines for the nutrition facts panel, the ingredient statement and allergen declaration, the nutritional claims, the statement of identity, the net contents statement, the type size and placement requirements for the label, and combinations thereof. For example, packaging *cannabis* products for consumption as food must conform to rigorous requirements by federal and state agencies and boards. By utilizing certain embodiments of the disclosure, one can save time and avoid costly mistakes as a result of improperly labeled food products. By utilizing certain embodiments of the disclosure, a professional can review and provide direction, and guidance for compliance with regulatory guidelines. In another example, labeling guidelines include, without limitations, guidelines for human prescription drug and biological products, such as active components, possible adverse reactions and contraindications.

In certain embodiments of the disclosure, a *cannabis* product received from any one or more of the sources described above can be subjected to a variety of testing protocols to determine the appropriate labelling information and prepare labels or reports for compliance with *cannabis* product guidelines from federal and state agencies and boards. For example, without limitations, different *cannabis* products can be consumed in different ways like smoking, vaporizing, eating a food product, drinking a liquid product, or utilizing injectable, sublingual or topical formulations. Labeling *cannabis* products for each of these consumption modalities will require detailed testing regarding the quality and quantity of desired components and undesired components. Certain embodiments of the disclosure include methods and systems to display on *cannabis* products received from any one or more sources described above, a plurality of identification information associated with the *cannabis* products. For example, by utilizing certain embodiments of the disclosure, one can develop the appropriate label or report required for the labeling or packaging necessary to prepare *cannabis* products for consumption. Certain embodiments of the disclosure result in the production of an appropriate nutrition facts panel for a *cannabis* product, including without limitation, the appropriate format and the contents for the panel as required by the regulatory agency or board, like the chemical analysis, the calorific analysis, the ingredient analysis, and combinations thereof. Other identification information associated with the *cannabis* products include source of the *cannabis* products, the particular strains of the *cannabis* plant, and the quality and quantity of desired components in the *cannabis* product. Information on the label can also include the various diseases that can be treated or mitigated using the *cannabis* products, such as but not limited to depression, pain, nausea, headaches, insomnia, glaucoma, epileptic seizures, inflammatory bowel diseases, lupus, arthritis, Parkinson's disease, post-traumatic stress disorders, and muscle spasms. These diseases can be acute or chronic in nature. Information on the label can also include one or more beneficial effects associated with the use of *cannabis* products, such as relief from anxiety or pain, improvements in lung health, lessen side effects of other drug treatments, and increase the effectiveness of other drug treatments. In certain embodiments of the disclosure, a user can access a database of *cannabis* products and receive information regarding the *cannabis* products, the nutritional analysis, an efficacy profile, the source of the ingredients, and details regarding the producers, processors, and sales entities associated with the *cannabis* product.

Certain embodiments of the disclosure also include labeling of the *cannabis* products with one or more visual indicators associated with the quality and quantity of desired components in the *cannabis* products. Certain embodiments of the disclosure also include labeling of the *cannabis* products with one or more visual indicators associated with each of the specified ranges of quantity of desired components in the *cannabis* product. Concentration includes, for example, the amount of a particular chemical component as compared to all others from oils, and plants products. The concentrations may be expressed, for example, in one or more of the following ways: percentage of weight/weight; percentage of volume/weight; percentage of volume/volume; percentage of weight/volume; percentage of particular chemical component/total active pharmaceutical ingredients (API(s)); and percentage of API(s)/total chemical component(s). Embodiments of the disclosure can also be based on *cannabis* plant derived-components or based on cannabinoids in a product. For example, as shown in Table 1, an edible product made from the *cannabis* strain popularly called Pineapple Express contains moderate levels of tetrahydrocannabinol (THC) but low levels of cannabidiol (CBD) and cannabinol (CBN). For example, as shown in Table 2, a *cannabis* product intended for consumption as a vaporizer or smoke, like a *cannabis* concentrate made from the *cannabis* strain popularly called Purple Babba Kush contains high levels of tetrahydrocannabinol (THC) but low levels of cannabidiol (CBD) and cannabinol (CBN). Tables 1 and 2 are exemplary examples and in no way limit embodiments of the disclosure. Other components that can be analyzed and indicated on the labels of the *cannabis* products include but are not limited to tetrahydrocannabivarin (THCV), cannabichromene (CBC), and cannabicyclol (CBL). Visual indicators can be bars, charts, graphs, symbols, codes or other graphical representations to indicate the relative concentration of one or more components in a *cannabis* product. Visual indicators can also indicate the efficacy or potency of the particular *cannabis* product to treat or mitigate particular illnesses or diseases. Embodiments of the disclosure can further include, for example, a reference standard calculated for each *cannabis* strain as understood by those skilled in the art and from there a percent (%) value from 0 to 50 percent can be assigned to each of the *cannabis*' API components. (With 0 being the lowest to 50 being the highest concentration % values, along with a moderate/medium concentration in the middle.) Embodiments of the disclosure allow consumers to make educated decisions regarding which products to consume or purchase based on the desired symptomatic relief or desired beneficial health effect.

TABLE 1

Major Components of Edible *Cannabis* Products from *cannabis* strain - Pineapple Express.

| Major Components | Low Concentration | Moderate Concentration | High Concentration |
|---|---|---|---|
| % THC |  |  | 18% |
| % CBD | 0.19% |  |  |
| % CBN | <0.05% |  |  |

TABLE 2

Major Components of *Cannabis* concentrates consumed through use of vaporizers.

| Major Component | Low Concentration | Moderate Concentration | High Concentration |
|---|---|---|---|
| % THC |  |  | 26% |
| % CBD | 0.19% |  |  |
| % CBN | <0.05% |  |  |

By way of example, an embodiment of the disclosure can include an online *cannabis* testing system or a home kit testing system. An embodiment of this system includes one or more indicators/processors, an input/output unit or apparatus adapted to be in communication with the one or more processors, one or more *cannabis* databases in communication with the one or more processors or stand-alone apparatus to store and associate a plurality of regulatory guidelines with a plurality of measurements of quality and quantity of desired components and undesired components in a *cannabis* product, one or more electronic interfaces positioned to display an online user report or apparatus readout and defining one or more *cannabis* user interfaces; and non-transitory computer-readable medium positioned in communication with the one or more processors and having one or more computer programs stored thereon. The computer program includes a set of instructions that when executed by one or more processors cause the one or more processors to perform operations of generating the *cannabis* user interface to display to an user thereof one or more online *cannabis* user reports, the *cannabis* user interface allowing an input of a plurality of information associated with the user or with the *cannabis* product, determining whether the *cannabis* product meets the regulatory guidelines responsive to receiving the plurality of information associated with the user or with the *cannabis* product and information from the one or more *cannabis* databases, associating the plurality of regulatory guidelines with the plurality of measurements of quality and quantity of desired components and undesired components in a *cannabis* product, and outputting to the one or more *cannabis* user interfaces the one or more online *cannabis* user reports, the *cannabis* user reports including one or more of the plurality of information associated with the user or with the *cannabis* product, and one or more of the plurality of measurements of quality and quantity of desired components and undesired components in a *cannabis* product.

Certain embodiments of the disclosure integrate the testing results from *cannabis* processing centers with other information associated with the *cannabis* products and thereby address a public need for standardized information and regulation of legal *cannabis* products. Certain embodiments of the disclosure allow for tracking the identity, quality and quantity of raw materials, and the desired and undesired components in them, as the raw materials—the *cannabis* plants—are processed to finished *cannabis* products, packaged and labeled for wholesale and retail outlets. Certain embodiments of the disclosure allow for research or public use, federal agencies or state regulatory agencies to regulate consumption and provide further guidelines for testing and regulation as well as allow for consumers to be fully informed of the product they purchase or consume. Package labeling for regulation and accurate information requires the integration of several analytical testing to provide the data and information needed to appropriately certify a product. Certain embodiments of the disclosure provide governing agencies a way of monitoring and regulating legal distribution of *cannabis* products. By a way of example, an embodiment of the disclosure can include measuring the quality or quantity of THC (or other cannabinoids) in edible products and certifying or producing a label that indicates that that the tested product meets appropriate regulations such as having no more than 100 milligram of THC in an edible *cannabis* product.

In certain aspects, all testing protocols that detect the quality and quantity of desired components and undesired components in the *cannabis* products can be carried out in one or more *cannabis* processing centers for research purposes, public use purposes, or a combination thereof. These centers are equipped to receive samples of *cannabis* products from a plurality of users, subject the samples of *cannabis* products to the appropriate testing protocols, and deliver a plurality of information associated with the user or with the *cannabis* product. Testing protocols that can be housed in a *cannabis* processing center include without any limitation, one or more of the following: microbiological testing, food testing, acidified food testing, liquid testing, pathogen testing, additional testing services, or combinations thereof. Testing protocols for a *cannabis* product can be performed by one or more *cannabis* processing centers. For example without limitation, one *cannabis* processing center can perform a subset of the testing protocols like microbiological testing and pathogen testing, while another processing center can perform food and nutritional testing on the same samples. A *cannabis* processing center can be remote from or house the one or more *cannabis* databases that store a plurality of regulatory guidelines with a plurality of measurements of quality and quantity of desired components and undesired components in the *cannabis* products. A *cannabis* processing center can also be remote from or house the equipment and personnel required to perform the testing protocols to determine whether the *cannabis* products meet the regulatory guidelines. A *cannabis* processing center can also be remote from or house the equipment and personnel required to perform the testing protocols to determine the quality and quantity of desired components and undesired components in the *cannabis* products. The *cannabis* processing centers can be certified testing centers that comply with the guidelines and regulations from state or federal control boards or agencies including but not limited to the US Department of Agriculture, the Food and Drug Administration, and the Drug Enforcement Agency.

According to an exemplary embodiment of the disclosure, the *cannabis* processing center includes one or more labs that have good laboratory practices and current good manufacturing practices set by federal or state agencies as understood by those skilled in the art to performing quality testing and quality assurance procedures. Embodiments of the disclosure including analyzing *cannabis* and cannabinoid products for research studies to test and set parameters for third parties, such as government agencies, for grant awards, public safety, quality control and quality assurance purposes.

FIG. 1 is an illustration of an exemplary embodiment of the methods of the disclosure. In one embodiment, the method involves the use of *cannabis* testing procedures 101. In a further embodiment, the *cannabis* testing procedures can be housed in a *cannabis* processing center. Users of this embodiment of the disclosure submit samples of their *cannabis* products for testing. These *cannabis* testing procedures 101 detect the quality and quantity of desired components and undesired components in the *cannabis* products. Testing protocols include without any limitation, one or more of the following: microbiological testing, food testing, acidified food testing, liquid testing, pathogen testing, additional testing services, or combinations thereof. For example, users of *cannabis* smoking products 102 can submit their samples for quality control and quality assurance testing 103. In certain embodiments of the disclosure, users of *cannabis* pharmaceutical products 104 can submit their samples for quality control and quality assurance testing 103. In certain embodiments of the disclosure, users of *cannabis* food and beverage products 106 can submit their samples for quality control and quality assurance testing 107. In certain embodiments of the disclosure, users of *cannabis* medicinal or health products 105 can submit their samples for quality control and quality assurance testing 107.

In certain embodiments of the disclosure, users can access a variety of information, recommendations, and advisory reports 109 relating to labeling and regulatory compliance aspects of *cannabis* products submitted for testing. Users of certain embodiments of the disclosure can access a variety of information and reports 110, including, but not limited to, reports regarding the origin and processing records, the chemical and biological contents of the *cannabis* products submitted for testing. Certain embodiments of the disclosure include users like federal and state agencies or boards accessing the information to generate reports 108, including, but not limited to, reports regarding the various *cannabis* products available in the various industries, production and processing volumes of the various products, the producers of the various products, and their compliance to the laws and regulatory guidelines. Information from certain embodiments of the disclosure, like the database with all the product data, is important in helping producers, processors, and sellers sustain or improve their product and their performance in the supply chain, and for making decisions regarding which producers, processors, and sellers can be relied on to meet specified requirements of the consumers, or the appropriate regulatory agencies or boards. In certain embodiments of the disclosure, a *cannabis* product received from any one or more of the sources described above can be subjected to a variety of testing protocols to help federal and state agencies and boards with conducting safety assessments and recalls of the *cannabis* products, and other enforcement actions.

Figure 2:
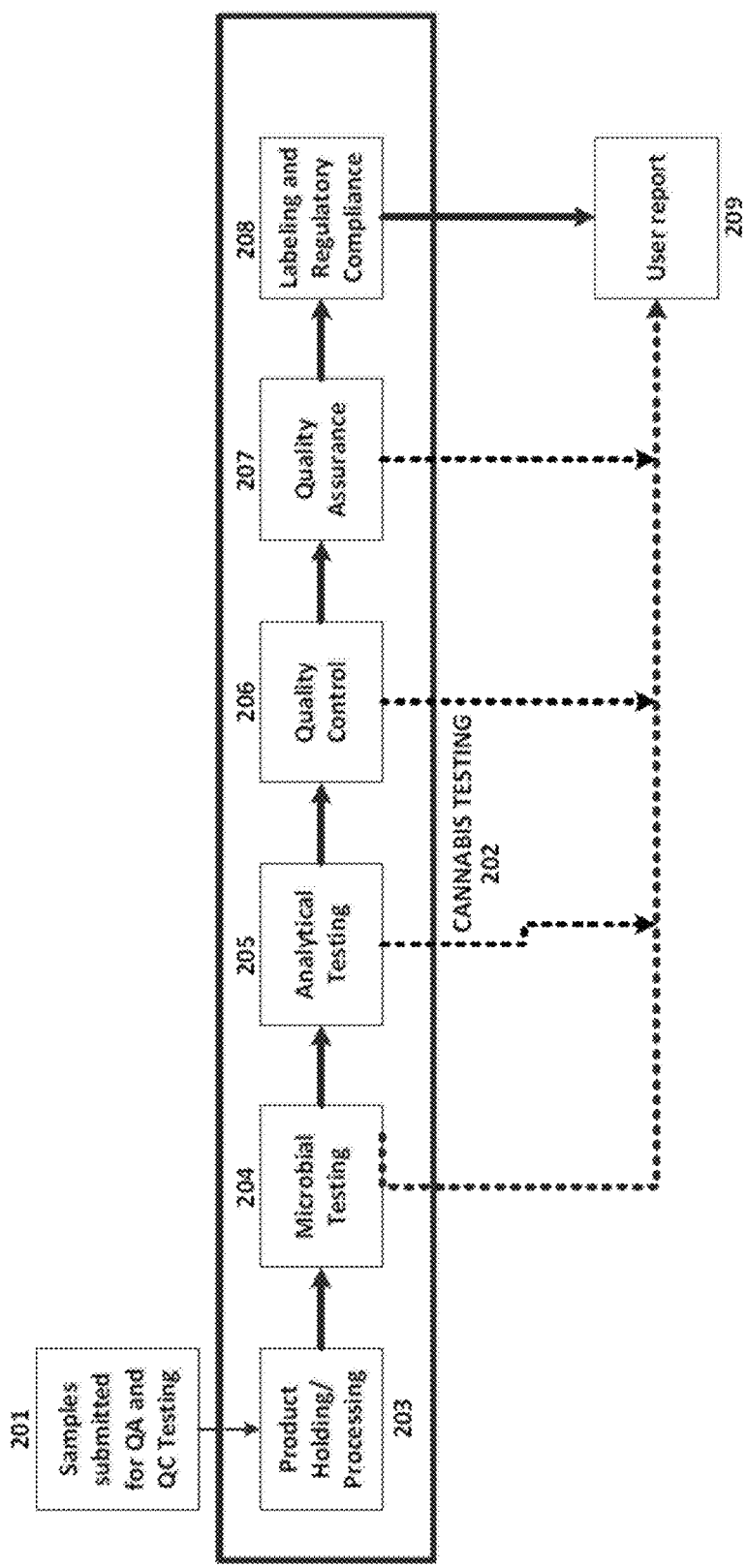
FIG. 2 is a schematic block diagram of an exemplary method according to an embodiment.

FIG. 2 is an illustration of an exemplary embodiment of the methods of the disclosure. Samples are submitted by users 201 for quality control testing, quality assurance testing, or both quality assurance and quality control testing. In certain embodiments of the disclosure, these samples can be initially processed 203 for the appropriate testing procedures 202. In other embodiments of the disclosure, the samples can be directly utilized in any of the testing procedures 202 that detect the quality and quantity of desired components and undesired components. Testing protocols include without any limitation, one or more of the following: microbial testing, analytical testing, food testing, acidified food testing, liquid testing, pathogen testing, additional testing services, or combinations thereof. In certain embodiments of the disclosure, these samples are subjected to microbial testing 204 that detect, for example without limitations, the presence of microorganisms, the type of microorganisms, the quantity, or combinations thereof.

In certain embodiments of the disclosure, these samples are subjected to analytical testing procedures 205 that detect the quality and quantity of desired components and undesired components. Analytical tests, for example without limitations, can include extractables/leachables studies, reference standard characterization, structural elucidation of target/lead compounds, structural elucidation of unknowns, impurity and degradation studies, identification and characterization of the quantity of chemical components, synthesis and purification of impurities and degradation products, and elemental analysis of the *cannabis* products.

In certain embodiments of the disclosure, these samples are subjected to quality control tests 206. Quality control testing ensures that *cannabis* products of a high quality, good safety profile and with the desired potency are supplied to the public, for their good health and for the economic benefits derived from trade of safe *cannabis* products. In certain embodiments of the disclosure, the samples subjected to quality control tests range from the raw materials to finished products. In certain embodiments of the disclosure, testing can be conducted to ensure that products at each step of the *cannabis* product supply chain meet quality and safety standards specified by the appropriate regulatory agencies or boards.

In certain embodiments of the disclosure, these samples are subjected to quality assurance tests 207. Quality assurance is a comprehensive program designed to ensure that one or more of the cultivation, production, processing, or sales of the *cannabis* products, or combinations thereof, meet a minimum standard of quality. In certain embodiments of the disclosure, this quality assurance ensures that the products from a particular producer, processor or seller meet the minimum standards set by the regulatory agencies or boards. In certain embodiments of the disclosure, this quality assurance ensures that the products from a particular producer, processor or seller meet the appropriate standards set by the regulatory agencies or boards. In certain embodiments of the disclosure, this quality assurance ensures that the products from a particular producer, processor or seller are consistent with the labeling on the product.

In certain embodiments of the disclosure, these samples are analyzed for their compliance with labeling and other regulatory guidelines 208. In certain embodiments of the disclosure, *cannabis* products are analyzed for compliance with guidelines for the nutrition facts panel, the ingredient statement and allergen declaration, the nutritional claims, the statement of identity, the net contents statement, the type size and placement requirements for the label, and combinations thereof.

In certain embodiments of the disclosure, users can access a variety of information, records, recommendations, and advisory reports, collectively described as user reports 209, resulting from the testing of the *cannabis* products. Users of certain embodiments of the disclosure can access a variety of information and reports 209, including, but not limited to, reports regarding the origin and processing records and the chemical and biological contents of the *cannabis* products submitted for testing. Certain embodiments of the disclosure include users like federal and state agencies or boards accessing the information to generate reports 209, including, but not limited to, reports regarding the various *cannabis* products available in the various industries, production and processing volumes of the various products, the producers of the various products, and their compliance to the laws and regulatory guidelines.

Certain embodiments of the disclosure involve the systems, computer-readable program product, and related computer-implemented methods to obtain information from the users and generate *cannabis* user reports, according to embodiments of the present disclosure as discussed above. These embodiments can be implemented using one or more computers, one or more servers, one or more databases, and one or more cloud computing configurations, and one or more communications networks. Certain embodiments of the disclosure include a system for collecting a plurality of information related to a *cannabis* product and maintaining a registry. The plurality of information includes but is not limited to information regarding *cannabis* production facilities, *cannabis* strains, *cannabis* products, associated test results and compliance certificates, *cannabis* processing and distribution systems, and ultimate consumers. The plurality of information can also include information from inventory tracking software, like Colorado's Marijuana Inventory Tracking Solution (MITS).

Certain embodiments of the disclosure include a system with one or more remote electronic interfaces configured to receive selection parameters entered by user and display a plurality of information related to one or more *cannabis* products. The system also has one or more databases that acquire and store the plurality of information related to one or more *cannabis* products and one or more processors in communication with the one or more databases. These processors are configured to acquire selection parameters entered by user through remote electronic interfaces, generate a data package from the plurality of information related to the *cannabis* product in the database responsive to the selection parameters entered by user and display the data package to the user responsive to the selection parameters entered by user through remote electronic interfaces.

Embodiments of the disclosure can include, for example, analyzing one or more *cannabis* products to determine the quality and quantity of desired components and undesired components in the one or more *cannabis* products using one or more of the following, for example: cannabinoid profiling, microbiological testing, analytical testing, food testing, acidified food testing, liquid testing, pathogen testing, quality control testing, quality assurance testing, or combinations thereof. Embodiments can further include, for example, determining concentration of one or more cannabinoids and determining the appropriate regulations for the *cannabis* products such as the relevant state regulations regarding the sale or consumption of *cannabis* products. Embodiments of the disclosure can further include comparing measurements of the quality and quantity of desired components and undesired components in the one or more *cannabis* products against state regulations for consumption of the one or more *cannabis* products and generating a report, for example that includes if the *cannabis* product satisfied the appropriate regulations.

Figure 3:
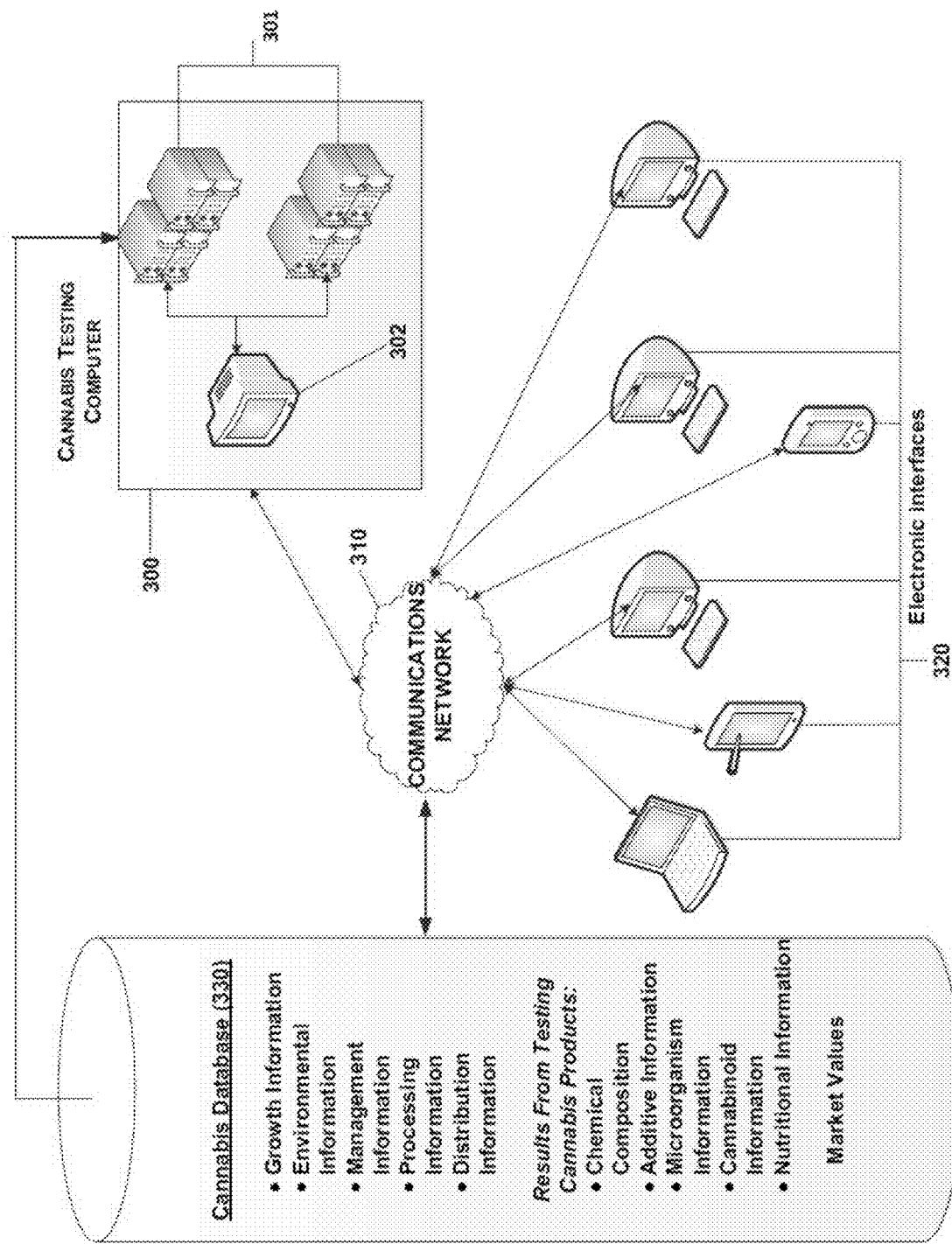
FIG. 3 is a schematic diagram of an exemplary system according to an embodiment.

FIG. 3 is an illustration of a system that is an exemplary embodiment of the disclosure. Such a system can include, for example, a communications network 310, a plurality of electronic interfaces 320, *cannabis* testing computer system 300, associated interfaces 302, associated servers 301, and a database 330. One or more entities can operate or control the *cannabis* testing computer system 300 that includes associated interfaces 302 and associated servers 301, with communication to a database 330, and a plurality of electronic interfaces 320. The communications network 310 can include a telephony network, a wireline network, a wireless network, a wide area network, a local area network, an infrared network, a radio-frequency network, an optical network, or any cloud computing configurations, or any other communications network now or hereinafter created as is known and understood by those skilled in the art. Each of the plurality of electronic interfaces 320 allows a human user, such as a producer, a processor, or a consumer, to interact with the *cannabis* testing computer system 300. Each of the electronic interfaces 320 allows such a human user, for example, to input information associated to one or more *cannabis* products as is described herein with respect to the *cannabis* testing system. Each of the electronic interfaces 320 allows such a human user, for example, to receive the *cannabis* user reports, and to access appropriate information from the *cannabis* testing system.

The reports from the *cannabis* testing system may be received by a user in a variety of formats, including, but not limited to, paper print-outs, graphical or text displays on a computer or mobile device, electronic messages like an e-mail or text, and other equivalent formats. The output from a *cannabis* testing system can include other techniques including updating a record in a database, updating a spreadsheet, and sending instructions and/or data to specialized software, such as an application on a mobile device, or combinations thereof. In other embodiments, the output from a *cannabis* testing system may include formats and reports stored on computer readable medium (such as a CD, DVD, USB flash drive, stand alone, or other removable storage device, computer hard drive, or computer network server, etc.). The output from a *cannabis* testing system, particularly those stored on computer readable medium, can be part of a database, which may optionally be accessible via the internet, such as a database of information regarding various *cannabis* products, the associated producers, processors or sellers stored on a computer network server. The database may be a secure database with security features that limit access to information regarding various *cannabis* products, such as to allow only authorized users to view them.

According to various exemplary embodiments of the present disclosure, the database 330 can be any database structure as is known and understood by those skilled in the art. The databases discussed herein, including database 330, can be, for example, any sort of organized collection of data in digital form. Databases, including database 330, can include the database structure as well as the computer programs that provide database services to other computer programs or computers, as defined by the client-server model, and any computer dedicated to running such computer programs (i.e., a database server). An exemplary database model, for example, is a Microsoft SQL Server 2014 CTP2 or SQL Server 2012, or SQL Server 2008 R2. Databases can include a database management system (DBMS) consisting of software that operates the database, provides storage, access, security, backup and other facilities. DBMS can support multiple query languages, including, for example, SQL, XQuery, OQL, LINQ, JDOQL, and JPAQL. Databases can implement any known database model or database models, including, for example, a relational model, a hierarchical model, a network model, or an object-oriented model. The DBMS can include Data Definition Language (DDL) for defining the structure of the database, Data Control Language (DCL) for defining security/access controls, and Data Manipulation Language (DML) for querying and updating data. The DBMS can further include interface drivers, which are code libraries that provide methods to prepare statements, execute statements, fetch results, etc. Examples of interface drivers include ODBC, JDBC, MySQL/PHP, FireBird/Python. DBMS can further include a SQL engine to interpret and execute the DDL, DCL, and DML statements, which includes a compiler, optimizer, and executor. DBMS can further include a transaction engine to ensure that multiple SQL statements either succeed or fail as a group, according to application dictates. DBMS can further include a relational engine to implement relational objects such as Table, Index, and Referential integrity constraints. DBMS can further include a storage engine to store and retrieve data from secondary storage, as well as managing transaction commit and rollback, backup and recovery, etc.

Data stored in fields of the databases can be updated as needed, for example, by a user with administrative access to the database to add new data to the libraries in the database as they become supported. It will be appreciated by those having skill in the art that data described herein as being stored in the databases can also be stored or maintained in non-transitory memory and accessed among subroutines, functions, modules, objects, program products, or processes, for example, according to objects and/or variables of such subroutines, functions, modules, objects, program products or processes. Any of the fields of the records, tables, libraries, and so on of the database can be multi-dimensional structures resembling an array or matrix and can include values or references to other fields, records, tables, or libraries. Any of the foregoing fields can contain either actual values or a link, a join, a reference, or a pointer to other local or remote sources for such values.

Database 330 can be, for example, a single database, multiple databases, or a virtual database, including data from multiple sources, for example, servers on the World Wide Web. The *cannabis* database 330 can contain several types of data, including, but not limited to, plant information associated with the *cannabis* products, growth information of the plants, environmental information, plant management information, raw material processing information, *cannabis* product distribution information, and results from testing *cannabis* products. These results from testing *cannabis* products can include, without limitations, chemical composition, additive information, microorganism information, cannabinoid profile, nutritional information, and market information. In certain embodiments of the disclosure, the market information can include historical sales data, sales projection data, and real-time market values for raw materials and processed *cannabis* products in a variety of industries. The plant information associated with the one or more *cannabis* products in the one or more *cannabis* databases includes one or more of: *cannabis* strain, source of seeds, genotype and phenotype of the plants associated with the one or more of the *cannabis* products, and combinations thereof. The environmental information associated with the one or more *cannabis* products in the one or more *cannabis* databases includes one or more of: germination conditions, location, temperature, water, exposure to light, and combinations thereof. The plant management information associated with the one or more *cannabis* products in the one or more *cannabis* databases includes one or more of: pesticide use, fertilizer use, growth pattern control, and combinations thereof. The consumer information associated with the one or more *cannabis* products in the one or more *cannabis* databases includes purchase patterns, disease indication, diagnostic test results, dose, dosage, time frame of administration, prescribing healthcare professional's data, adverse reaction reports, contraindication report, and therapeutic efficacy. Database 330 can be the inventors' proprietary database or one populated with data from publicly available databases or a combination thereof.

According to various exemplary embodiments of the present disclosure, for example, and as illustrated by FIG. 3, the *cannabis* database 330 can be part of a data warehouse. Such a data warehouse may include other databases, for example, a user database, an administration database, content from or links to other public databases, a regulatory guidelines database, and/or a sales database. The user database can be configured, for example, to store any data related to user information, including user names, user addresses, state or federal authorization information, payment records, data related to user's products or consumption needs, and any other information related to a user, as is known and understood by those skilled in the art.

Figure 4:
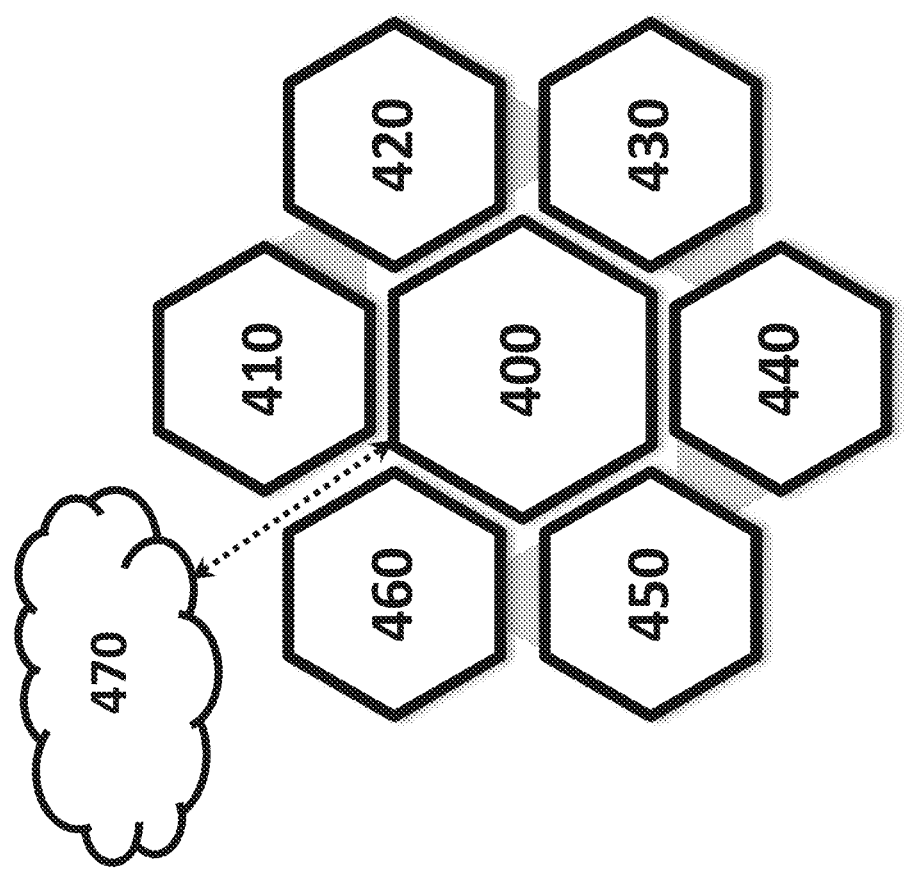
FIG. 4 is a schematic block diagram of an exemplary system according to an embodiment.

Embodiments include a system for managing the *cannabis* product from seed to treatment outcome. As shown in FIG. 4, the system has a general flow through modules that represent stages of information management. The first is the seed module 410 where profiling and characterization of the seed takes place. This characterization includes genetics and multi-omics to provide a fingerprint for the *cannabis* product(s) that is/are generated. The seed module 410 is vital for traceability and reproducibility of *cannabis* products. The second module is the agriculture module 420 where monitoring/profiling occurs through IT integration with agricultural tools for data collection and tracking. There are tools for monitoring outside plots (typically 0.5 to 1 acre plot), or indoor cultivation, that monitors agricultural parameters that include temperature, humidity, pressure, along with seed, soil and plant markers for profiling and detailing the growth and development of the *cannabis* product. The next module is the product testing module 430 where either the crop or product is processed and tested. The product testing module 430 provides lab solutions management that include one of more analytic techniques like liquid chromatography or gas chromatography (LC/GC), analysis software, data management and enhanced security feature for testing crop/product and determining if product is safe for release to patients. The next module is the product release module 440 where a product has been certified and labeled appropriately and reports generated that characterizes the product and its correlation to the seed from whence it came. The product release module 440 manages reports for distributors, pharmacists, physicians, regulators and other pertinent personnel. The system continues with a patient administration module 450 that includes pharmaceutical formulation, compounding, kits, packaging and imaging conjugation. The patient administration module 450 will be vital to manage prior for appropriately guiding the next treatment outcome module 460. The next module is the treatment outcome module 460 where administration of the *cannabis* product to a patient is monitored and treatment outcome is validated. The treatment outcome module 460 involves pharmacists, physicians and patients with data management integration that utilizes Federal and State regulated guidelines for patient health information to monitor and determine treatment outcomes. The treatment outcome module 460 will also provide researchers with both validation information and new information to guide the next steps in translational research. In some embodiments, the seed module 410, the agriculture module 420, the product testing module 430, the product release module 440, the patient administration module 450, and the treatment outcome module 460 can be arranged in any order.

Each module provides information to a given product that allows for correlating any given step with the other processes associated with that given product. These modules are managed by information integration across a blockchain system to provide the overall comprehensive data for providing any *cannabis* product. In some embodiments, data collected in each module can be uploaded to a blockchain identifier (BCI) unit 400. As a result, each module can download and share data from other modules that were uploaded to the BCI unit 400. In addition, data uploaded to the BCI unit 400 from individual modules can be uploaded to a cloud server 470. In other embodiments, data collected in each module can be uploaded directly to the cloud server 470. In some embodiments, the BCI unit 400 and the cloud based server 470 are integrated to a single unit.

Embodiments include systems and methods of supplying a *cannabis* product through a blockchain platform. The systems and methods include tracking and testing the seed, the planting, the crop, the product, the treatment and the distribution for ensuring quality control and quality assurance for a safe product for human administration. In some embodiments, data collected from each module are uploaded to the BCI unit 400 and/or the cloud server 470, where the BCI unit 400 and/or the cloud server 470 can generate a unique BCI in a certain predetermined period. The BCI can include a blockchain that an individual block further includes timestamps and hash values. The BCI can include a block that includes all data uploaded by each module. The block may also include a current hash value which is generated from the data uploaded by each module in the current predetermined period. The block may also include a past hash value of a previous block generated immediately before the current predetermined period. This way, the past hash value serves as a link (hence the term "chain") between the previous block and the current block, forming a blockchain. Each block or the entire blockchain included in the BCI can be downloaded by each module. This way, each module can download a reduced sized block or blockchain than downloading the entire data uploaded to the BCI unit 400 and/or the cloud server 470.

The seed module 410 includes systems and methods for acquiring data of a seed. The systems and methods include obtaining a seed from a source and profiling that seed. Profiling includes genetic sequencing and multi-omic analysis to determine properties of a given strain producing a data set. The source and the data set generated from profiling can be uploaded to the BCI unit 400 to generate a unique BCI. The source and the data set generated from profiling can be uploaded to a cloud server 470 associated with the assigned BCI.

Several characteristics and properties of medical *cannabis* begin with the seed and its profile. Embodiments include determining the genetic sequence of the *cannabis* seed to characterize a given strain. An approved grower will submit seeds for genetic analysis and further characterization, such as multi-omic analysis. The genetic profile is used as an identifiable marker for the given development of a particular crop of *cannabis* plants. Once the seed is characterized by its genetic profile, it is then assigned a unique identification code that is used subsequently for accessing and verifying purchases and transfers associated with that seed and its progeny.

In certain embodiments of the disclosure, a seed profile can contain information that includes genetic sequence, germination, genetic purity, protein and enzyme markers, genotyping, phenotyping, hybridization, genus and species determination to name a few. Profiling may further include plant tissue residue analysis, genetically modified events detection, seed treatment applications detection, seed stability and storability, seed quality assurance development, seed plantability assessment and seedling growth rates. The profile information is obtained from seed testing and/or an existing seed bank that has characterized the seed. Comparative testing can be performed on seeds with seed bank profiles in order to reconcile if there are differences in sequences that have not been previously characterized. Genetic strain determination is associated with seed profiling to allow for predicting, determining, characterizing and comparing cannabinoid product profile.

In certain embodiments of the disclosure, information associated with a variety of *cannabis* seeds is received from a breeder or a seed bank. Information regarding seeds corresponding to a single strain and a specific breeder or seed bank can be stored as a seed record on a blockchain-based transaction platform. Embodiments include a method of purchasing seeds of a specific strain of *cannabis*. The method includes the steps of receiving a request for seeds from a grower for a particular strain of *cannabis* or for seeds that would yield a particular *cannabis* product profile. Information regarding the growers can be stored as grower records on the blockchain-based transaction platform. In the next step, a particular seed record is identified in response to the request by comparing the request to the seed records stored on the blockchain-based transaction platform, and information from this seed record for satisfying the request is conveyed to the trusted grower. If the trusted grower wishes to proceed with a financial transaction to purchase seeds corresponding to the matched seed record, then he can proceed with a purchase. Any financial transaction between the trusted grower and breeder is stored as a purchase record on the blockchain-based transaction platform and connected to the seed record, grower record, and breeder or seed bank record. Embodiments of the system also allow trusted parties to redact information from the blockchain-based transaction platform, without causing the transaction platform to fail for its intended purpose. Embodiments include the ability to match and identify the appropriate strain that is stored in system. A grower may request from a breeder a particular strain of *cannabis* seed. The breeder can then validate the profile of the seed from the record generated from the profile that is stored in blockchain-based platform.

The agriculture module 420 includes systems and methods of acquiring plant management data for a particular crop cohort. An embodiment of the method would include manually inputting planting parameters data and/or collecting planting parameters data with a sensor. Planting data include soil moisture, air moisture, water added or irrigated, climate control or fluctuation, barometric pressure, light source, nutrients, and pesticides. Embodiments include systems that include devices configured to sense soil and weather parameters and generate soil and weather records. An example of a device includes a containment unit with detection sensors that detect soil data and planting parameters data. Sensors that send data to containment unit can be attached to agricultural tools for directly measuring the plants for needed parameters. Soil parameters include moisture consistency, nutrients content, microorganisms, and toxicants. Soil analysis is performed periodically from planting to harvest. The soil data and planting parameters data can be uploaded to the BCI unit 400 to generate a unique BCI related to the particular *cannabis* strain, the grower, the location, and other growth parameters. The soil data and planting parameters can be uploaded to cloud server 470 associated with the assigned BCI.

Many factors affect the outcome of crop growth and development that may enhance or impede *cannabis* production, particularly factors associated with the planting and farming process. Embodiments of methods and systems include sensors that detect soil moisture, air moisture, water received by the plants, climate control or fluctuation, barometric pressure, light source, nutrients, and pesticides. The planting of the seed data is dated and time stamped and manually inputted and uploaded to the blockchain record established for the strain of seeds planted. Initial parameters are also inputted such as addition of nutrients, amount of water, or soil analysis. Subsequently sensors are placed to detect and capture the day to day factors that facilitate seed germination and growth. With each detection, the data is uploaded to the BCI unit 400 and/or the cloud server 470.

A salient feature to the propagation of *cannabis* plants is the root to soil interface. The soil provides crucial nutrients and moisture necessary to maintain the steady progress to a fully bloomed plant. Likewise, the soil contains a microflora that has substantial interaction with the plant's roots that helps to direct growth. This region of the soil is known as the rhizosphere. Embodiments include identifying the profile of the soil, including moisture consistency, nutrients, microorganisms, pesticides and toxicants. The soil analysis can be accomplished by microorganism test analysis and the data inputted to the BCI unit 400 and/or the cloud server 470. Subsequently sensors are placed to detect day to day soil changes where each detection generates data that is uploaded to the BCI unit 400 and/or the cloud server 470.

In certain embodiments of the disclosure, the agriculture module 420 includes sensors that directly measure agricultural parameters for monitoring and tracking the growth and development of the plant. Tools and devices used in the agriculture module 420 can be IT-integrated such that the sensors can directly send the data to a blockchain-based platform, thus allowing monitoring and tracking during harvesting, processing and storing prior to lab testing.

Growing of *cannabis* plants can occur in both outdoor environments such as arable land or indoor setting. In many cases, indoor platform-based systems has been developed to enhance the ability to control planting parameters for consistency and to improve harvest baring outcomes. Furthermore asexual propagation using cloning is also being developed for consistent plant production. Embodiments of the disclosure include sensors capturing climate and environment factors for either outdoor planting or indoor planting. The sensors would capture the day to day climate and environmental controls or changes, which would generate data that is uploaded to the BCI unit 400 and/or to the cloud server 470. In certain embodiments of the disclosure, the agriculture module 420 includes growth analytics, which relate to the correlation and grouping of the profile of a given seed or product.

*Cannabis* plants are often profiled and categorized with simplified descriptions indicating the psychoactive effects of THC, however comprehensive profiling of *cannabis* plants is much more extensive and correlation to growth analytics is an important part of this analysis. The disclosure includes embodiments of correlating the growth analytics to the cannabinoid profile outcomes of *cannabis* plants.

The sensors include a modular unit with probes that measure various desired parameters, for example a probe that explicitly measure barometric pressure. The modular unit integrates with platform directly sending the data to blockchain-based platform. For outdoor plant operations, weather services are integrated for weather prediction and monitoring to further maintain record of anomalies or changes due to abhorrent or favorable weather patterns. The platform allows for manual input of information, where comparison of measured data can reconcile discrepancies. The overall agricultural module 420 provides for establishing data to be uploaded to a BCI unit 400 and/or to the cloud server 470 for stepwise tracking and monitoring from the agricultural process to human consumption. After the *cannabis* plants are harvested, the plants are processed to an end product. Depending on the use of the plants, the product can prepared to meet the medical, research, or recreational markets.

The product testing module 430 include systems and methods for comprehensive product testing, as disclosed in U.S. Pat. No. 9,632,069, is incorporated here by reference in its entirety. Data generated from the product testing module 430 can be uploaded to the BCI unit 400 to generate a unique BCI. The data generated from the product testing module 430 can be uploaded to a cloud server 470 associated with the assigned BCI.

Determining whether a cannabinoid product is safe for administration or consumption is one of the main purposes of an integrated comprehensive testing module, as it is the last line of defense prior to direct human administration. Safety profile, quality control, and quality assurance will be key to releasing a product for administration. Embodiments include a blockchain platform that includes blocks containing information from certain series of tests. Tests include microbiology/pathogens/mycotoxins, pesticides/toxicants, residual solvents/liquids, heavy metals, terpene profiling, and cannabinoid potency. The sequence of testing has priority, particularly when determining the whether a medical cannabinoid product is safe for human consumption. The system may use a pass or fail system based on standardization of allowed levels of substances. There are industry and governmental agency thresholds for desired and undesired components in foods and drugs that are not permissible for human consumption.

Embodiments include systems and methods of testing *cannabis* crop or product through a series of analytical testing including testing for microbes, pathogens and/or mycotoxins, toxicants, residual solvents and liquids, heavy metals, and the cannabinoid content and potency. An example method includes creating data records corresponding to results from the analytical testing. Data records can be uploaded to the BCI unit 400 to generate a unique BCI assigned to the particular *cannabis* strain, the grower, the location, and other growth parameters. The data records can be uploaded to a cloud server 470 associated with the assigned BCI.

Embodiments include systems and methods of microbial, pathogen, and toxin analysis of a *cannabis* crop or product. An example method includes the steps of analyzing a prepared sample of the *cannabis* products for microbiological, pathogenic and mycotoxin content, determining whether the sample is safe to continue with other testing. Safety parameters are set based on guidelines according to the Botanical Drug Development-Guidance for Industry outlined in FDA-CDER in December 2016 Pharmaceutical Quality/CMC Revision 1. At any stage of analysis, if the sample is deemed unsafe, then further analysis can be halted. If the sample is deemed safe, then further analysis is conducted. The data generated from the analysis is subsequently uploaded to the BCI unit 400 to generate a unique BCI assigned to the particular *cannabis* strain and trusted growers. The data records can be uploaded to a cloud server 470 associated with the assigned BCI.

Figure 5:
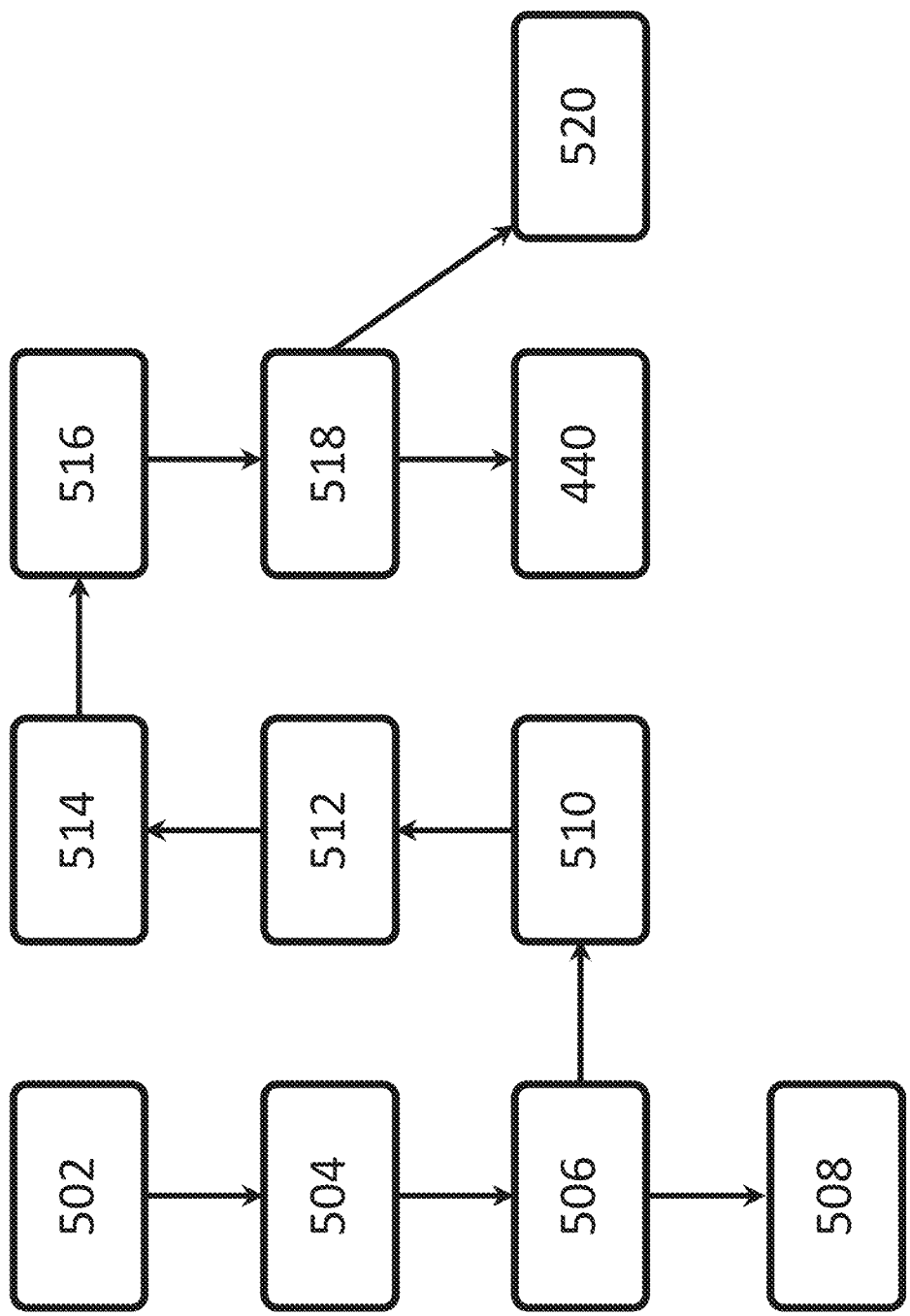
FIG. 5 is a schematic block diagram of an exemplary method according to an embodiment.

FIG. 5 shows an example sequence for the product testing module 430. In block 502, a sample with an assigned BCI is prepared. The sample can be transported to a testing location and prepared for the various testing modalities. For example, in block 504, the sample is weighed in a moisture sensitive balance to measure moisture content. Knowing moisture content provides the ability to determine if the sample is prone to growing mold, and the data generated in this step can be uploaded to the BCI unit 400 and/or the cloud server 470 to generate a unique BCI. In block 506, the sample is tested for microbes/pathogens/mycotoxins. For example, the testing can be administered by LC/MS and in a biosafety hood, and the data generated in this step can be uploaded to the BCI unit 400 and/or the cloud server 470 to generate a unique BCI. Samples are placed in a biosafety hood to determine microbial/pathogen growth. This step is very critical in the process in as much as a sample failing to have a safe microbiological/pathogenic/mycotoxin profile would immediately not continue with the rest of the series of testing. In block 508, if the sample fails to have a safe microbiological/pathogenic/mycotoxin profile, further testing is halted. This arrest in the testing series is conducted for two reasons: 1) the product is not safe for consumption and/or 2) the sample can contaminate the rest of the testing system. In block 510, if the sample has a safe microbiological/pathogenic/mycotoxin profile, the sample undergoes further testing for pesticides and toxicants. The testing can be administered by LC/MS; at which the data generated in this step can be uploaded to the BCI unit 400 and/or the cloud server 470 to generate a unique BCI. In block 512, the sample undergoes testing for residual solvents. The testing can be administered by GC/MS, where solvents used for extraction, synthesis or preparation may be within the content of the product; at which the data generated in this step can be uploaded to the BCI unit 400 and/or the cloud server 470 to generate a unique BCI. In block 514, the sample undergoes testing heavy metal content. The testing can be administered by ICP, and the data generated in this step can be uploaded to the BCI unit 400 and/or the cloud server 470 to generate a unique BCI. In block 516, the sample undergoes terpene profiling. The terpene profiling can be administered by GC-QP to determine other components beyond cannabinoid products that may be in the product; at which the data generated in this step can be uploaded to the BCI unit 400 and/or the cloud server 470 to generate a unique BCI. In block 518, the sample undergoes cannabinoid profiling for components and potency. The cannabinoid profiling can be administered by HPLC; at which the data generated in this step can be uploaded to the BCI unit 400 and/or the cloud server 470 to generate a unique BCI. While the embodiment described in FIG. 5 provides for generation of a unique BCI identifier at every step, other embodiments include generation of an identifier that builds on the preceding steps. Other embodiments include generation of an identifier at every step that captures the identifiers of the preceding steps.

Block 510 includes systems and methods for performing a toxicant analysis of a *cannabis* product. An example method may include preparing a sample of a *cannabis* product for analysis of toxicant content. Data generated from the analysis can be uploaded to the BCI unit 400 to generate a unique BCI assigned to a record identifying the *cannabis* strain. The data generated from the analysis can be uploaded to a cloud server 470 associated with the assigned BCI. Block 512 includes systems and methods for residual solvent and liquid analysis of a *cannabis* crop or product. An example method may include analyzing a prepared sample of the solvent and liquid content. Data generated from the analysis can be uploaded to the BCI unit 400 to generate a unique BCI associated with the given strain that produced the crop or product. The data generated from the analysis can be uploaded to a cloud server 470 associated with the assigned BCI. Block 514 includes systems and methods for heavy metal analysis of a *cannabis* crop or product. An example method may include analyzing a prepared sample of the heavy metal content. Data generated from the analysis can be uploaded to the BCI unit 400 to generate a unique BCI associated with the given strain that produced the crop or product. The data generated from the analysis can be uploaded to a cloud server 470 associated with the assigned BCI. Block 516 includes systems and methods for terpene profile and analysis of a *cannabis* crop or product. An example method may include analyzing a prepared sample of the terpene content. Data generated from the analysis can be uploaded to the BCI unit 400 to generate a unique BCI associated with the given strain that produced the crop or product. The data generated from the analysis can be uploaded to a cloud server 470 associated with the assigned BCI. Block 518 includes systems and methods for cannabinoid analysis of a *cannabis* crop or product. An example method can include analyzing a prepared sample for the cannabinoid content and potency. Data generated from the analysis can be uploaded to the BCI unit 400 to generate a unique BCI associated with the given strain that produced the crop or product. The data generated from the analysis can be uploaded to a cloud server 470 associated with the assigned BCI. Once the sample undergoes a series of testing, the product is determined whether it is safe for release to patients. If the sample is determined safe, the product can be released to patients, as shown for example via the product release module 440, as shown in FIGS. 4 and 5. Products from this representative sample is now certified and can be labeled as such on packaging from the party providing the product. Optionally, in block 520, the product can be stored over a period of three months to a year, or longer periods as desired. The shelf life of the product can be determined in this step. After the storage period, a sample from the stored product can be obtained and resubmitted to undergo the entire sequence of testing.

Block 520 includes systems and methods for testing the shelf life of a *cannabis* crop or product. An example method may include storing a sample for a desired period of time and testing for microbes, pathogens and/or mycotoxins; testing for pesticides and toxicants; testing for residual solvents and liquids; testing for heavy metals; analyzing the terpene profile; and testing the cannabinoid content and potency. At each testing step the data produced from testing can be uploaded to the BCI unit 400 to generate a unique BCI associated with the given strain that produced the crop or product. At each testing step the data produced from testing can be uploaded to a cloud server 470 associated with the assigned BCI.

Referring back to FIG. 4, the product release module 440 includes systems and methods for releasing a safe product. Once the sample is determined safe in the product testing module 430, the product can be released to patients. Products that pass the product testing module 430 is now certified and can be labeled as such on packaging from the party providing the product. Reports can be generated that characterizes the product and its correlation to the seed from whence it came.

In certain embodiments of the disclosure, the product release module 440 includes distributing the certified product to distributors, pharmacies, clinics, and hospitals. The product can be distributed to recreational retail stores. The product release module 440 manages reports for distributors, pharmacists, physicians, regulators and other pertinent personnel. Data produced from the product release module 440 can be uploaded to the BCI unit 400 to generate a unique BCI associated with the given strain that produced the crop or product. The data produced from the product release module 440 can be uploaded to a cloud server 470 associated with the assigned BCI.

The patient administration module 450 includes systems and methods for administering the released product to the patient. In certain embodiments of the disclosure, the patient administration module 450 includes administering the certified product to the patient. Data produced from the patient administration module 450 can be uploaded to the BCI unit 400 to generate a unique BCI associated with the given strain that produced the crop or product. The data produced from the patient administration module 450 can be uploaded to a cloud server 470 associated with the assigned BCI.

In certain embodiments of the disclosure, depending on the purpose of the product, a conjugate can be added to the product for imaging purposes. The conjugate is configured to chelate radioisotopes to the product for imaging. The product including the conjugate is administered to the patient and radioisotopic imaging is conducted. The imaging results can be used to validate the outcome of the treatment in the treatment outcome module 460.

Embodiments include systems and methods for administering and imaging a radiolabeled conjugated *cannabis* active pharmaceutical ingredient (API). An example method includes conjugating the *cannabis* API for administration with a cyclam derivative, radiolabeling the conjugated *cannabis* API, administering to a patient the radiolabeled conjugated *cannabis* API, and imaging the administered radiolabeled conjugated *cannabis* API through various imaging modalities. The imaging modalities include PET, SPECT, CT, MRI, Ultrasound or a combination thereof. Data generated from the analysis can be uploaded to the BCI unit 400 to generate a unique BCI associated with the given strain that produced the crop or product and associated with the given patient. The data generated from the analysis can be uploaded to a cloud server 470 associated with the assigned BCI.

The treatment outcome module 460 includes systems and methods for monitoring the administration of the *cannabis* product to a patient and validating the treatment outcome. Data produced from the treatment outcome module 460 can be uploaded to the BCI unit 400 to generate a unique BCI associated with the given strain that produced the crop or product and associated with the given patient. The data produced from the treatment outcome module 460 can be uploaded to a cloud server 470 associated with the assigned BCI.

Embodiments of the disclosure include collecting data from clinical outcomes post-cannabinoid product administration. Many factors surround the administration of the cannabinoid product that are required for determination and correlation of treatment outcomes. One of the first parameters are patient data, which includes but not limited to, genetic profiling, multi-omics profiling, known disease pathologies, current drug intake, demographic factors and environmental factors. Each patient is has a unique set of factors that impact treatment outcomes. Having access to the comprehensive validated data from seed to patient will allow for treatment outcomes to be appropriately correlated to an individual patient. The data for the patient is uploaded to the BCI unit 400 and/or the cloud server 470 that is HIPPA compliant. One of the salient features this blockchain method provides is a means of monitoring treatment efficacy through imaging modalities. The medical *cannabis* API is conjugated to cyclam derivative that allows for various imaging tracers to chelate to the composition and image the biodistribution of the medical *cannabis* API. Coupling the imaging modality provides a real-time method of determining if the medical *cannabis* uptake is occurring in the appropriate tissue regions or whether elimination of the product occurs. Advantageously, coupling the imaging modality can determine whether an improper CBD is administered or whether an adjustment of the dosage is necessary. If so, the physician may alter the administration. This treatment outcome information is uploaded to the BCI unit 400 and/or the cloud server 470 for the patient and correlated to the BCI of the strain that was collected.

Embodiments include systems and methods for profiling a patient. An example method includes acquiring and inputting certain patient data. Patient profile data includes but not limited to genetic profiling, multi-omics profiling, known disease pathologies, current drug intake, blood analysis, urine analysis, demographic factors, and environmental factors. Patient profile data can be uploaded to the BCI unit 400 to generate a unique BCI associated for the given patient compliance with Federal and State guidelines such as HIPPA guidelines. The patient profile data can be uploaded to a cloud server 470 associated with the assigned BCI.

Embodiments of the disclosure allow for the true correlation of patient data, patient modes of administration, and clinical outcomes of *cannabis* administration to be validated through monitoring cannabinoid uptake by imaging, in both the research setting and clinical setting. Treatment outcomes are not limited to human patients, but other animal subjects (in vivo and ex vivo) as well as in vitro assays. The conjugated cannabinoid provides a useful platform to explore cannabinoid products in a way that was not previously available. The connection of treatment outcome to seed and patient provides a holistic and tailored method of delivering medicine to a subject. The integrated information analytics can direct therapy, research, and safety profiles in both a patient centric format as well as a patient population format. This platform utilizes a precision medical approach to investigate and validate the connectivity of agricultural life science to product development and distribution and ultimately with human consumption and healthcare.

Embodiments of the disclosure include means of bridging product to patient centric treatment. In an embodiment, patient data from electronic medical records (EMR) systems is de-identified and supplied to the distributed validated *cannabis* system and this data includes medical review of patient profile and response to product administration. The EMR devices connect screening data with imaging data that validates patient response to administration. Devices provide access to the BCI information for a given product to know where the entire process that brought the *cannabis* product up to the point of administration and further connect that data with the patient's treatment outcome.

Data generated at every step of the method require processing, analysis and storage. Embodiments includes cloud based systems 470 for uploading and storing data generated at each step of the process with an association to a BCI. In certain embodiments of the disclosure, a computer implemented method for storing data on a cloud server 470 is disclosed. The cloud server 470 receives a request from a user or device to store data on the server. The cloud server 470 also receives from the user or device the BCI associated with that data. The server then determines processing and analysis based on preset algorithms for correlations. The server has the flexibility to allow for inputted algorithms for determining correlations. In some embodiments, the BCI unit 400 and the cloud server 470 are integrated to a single unit.

Embodiments include systems and methods for accessing, activating, bringing up the data associated with the BCI by an end user with predefined settings, and/or recording of the identity of an end user for any electronic device or computing device that is used by one or more users. The end user approaches an electronic device that can access the cloud server 470, the electronic device prompts the user for manual input of authentication, identification data and/or BCI, upon manually entering said authentication and or identification data into the electronic device, the authentication and or identification data is verified by the electronic device, then data transmitted to the electronic device from the cloud server 470. End users include, but not limited to the government, distributors, physicians, patients, pharmacists, growers, and researchers.

Embodiments include systems and methods for automating the accessing, activating, bringing up blockchain data associated with a BCI with end user predefined settings. An example system includes an electronic device, computing device, or non-transient medium including an electronic interface. The electronic interface communicates wirelessly with various electronic devices, and passes on the information to and from the electronic devices on a display. The display is part of the electronic device or is operatively connected to the electronic device to be accessed. The electronic device prompts the user to enter the password, display successful or unsuccessful login, and includes a memory controller that stores user information whereby the user is prompted on the display to enter a password if the information passed on from the electronic interface indicates that the user is an authorized user. The password is checked for validity and if valid the password is sent to the electronic interface for transmission and storage in the cloud server 470. The user is automatically allowed access to the electronic device and/or the predefined settings for that user is automatically loaded to the electronic device if the information passed on from the electronic interface indicates that the user has entered a valid password.

A key component to the integration process is the transmittal of data from devices to a cloud server 470 along with data being transmitted between devices and an interface to any given user. Embodiments of the disclosure include Internet of Things (IoT) for connecting multiple devices for capturing, transmitting, processing, analyzing, and storing data. The transmitted data is associated with a BCI for tracking and categorizing the data that is accessed at any interface. The process as described in FIG. 4 accentuates different access points of data collecting that may represent multiple devices sending data to the blockchain ledger for a given BCI. Information cannot be altered from the immutable ledger in the blockchain system, but only verified and validated. Security provision will be established that allows the appropriate entity to access the data or report needed.

Figure 6:
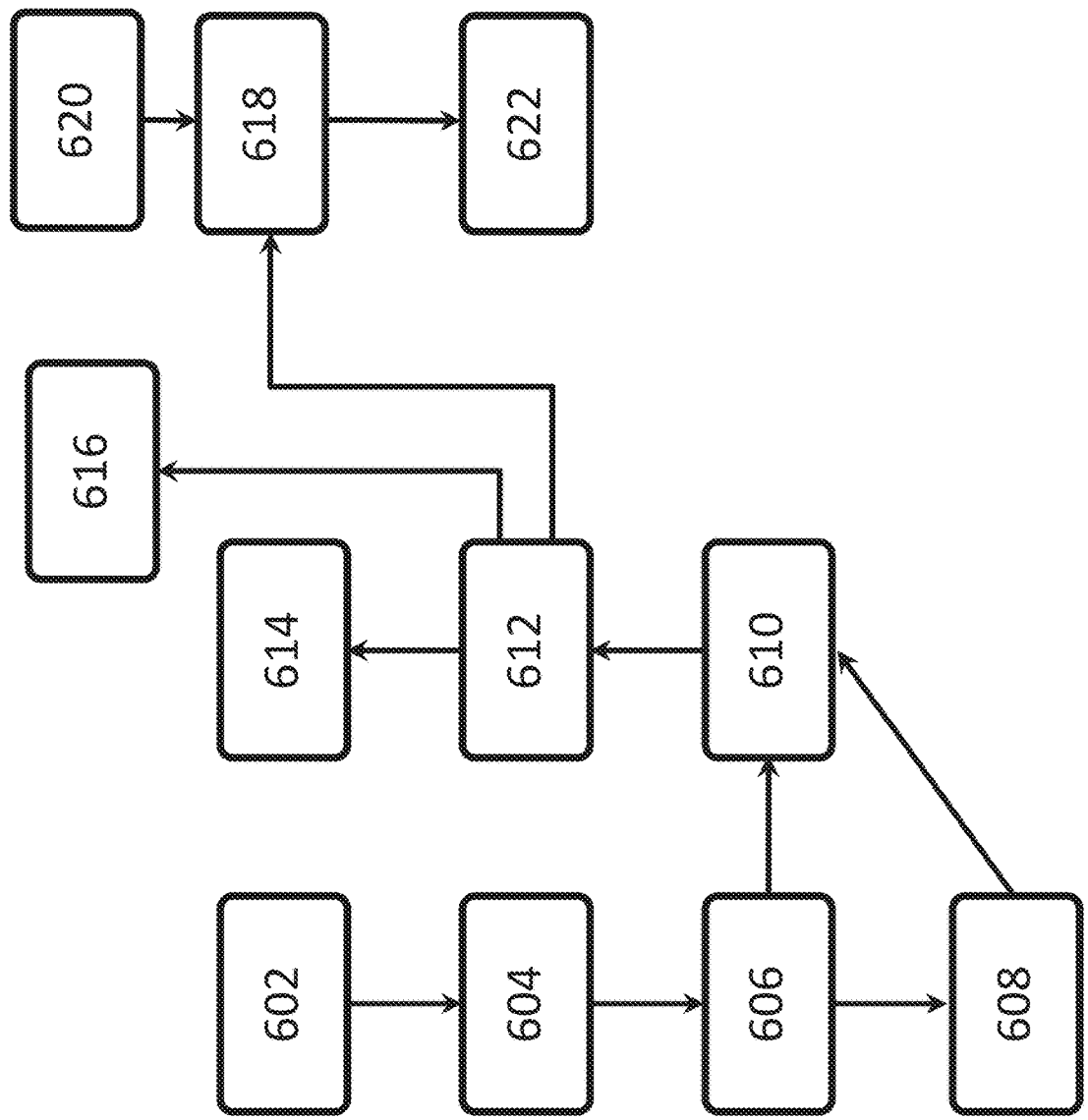
FIG. 6 is a schematic block diagram of an exemplary method according to an embodiment.

Embodiments include a distributed validated system for managing the *cannabis* product from seed to treatment outcome. FIG. 6 is a schematic representation of blocks created to manage information related to a *cannabis* product across a distributed validated system. Block 602 is created that contains the genetic profile of a seed used for production of a *cannabis* product. Block 602 is linked to block 604. Block 604 contains plant growth conditions of a crop used for production of the *cannabis* product and allows access to the information in the block 602. Block 604 is linked to block 606. Block 606 contains manufacturing information for production of the *cannabis* product and allows access to the information in the blocks 602 and 604. Block 606 is linked to block 608 and block 610. Block 608 contains storage information with regards to the *cannabis* product and allows access to the information in the blocks 602, 604, and 606. Block 608 is linked to block 610. This block 610 contains information from the testing of the *cannabis* product to determine quality and quantity of desired components and undesired components in the *cannabis* product using one or more of: cannabinoid profiling, microbiological testing, analytical testing, food testing, acidified food testing, liquid testing, pathogen testing, quality control testing, quality assurance testing, or any combinations of the foregoing. This block 610 also contains information about the concentration of one or more cannabinoids in the *cannabis* product. Block 610 allows access to the information in the blocks 602, 604, 606, and optionally 608. Block 610 is linked to block 612. Block 612 contains information about the *cannabis* product satisfying the appropriate regulations for consumption of the *cannabis* product, and allows access to the information in the blocks 602, 604, 606, 610, and optionally 608. Block 612 is linked to three blocks 614, 616, and 618. Block 614 contains information about the disposal of *cannabis* product that does not satisfy the appropriate regulations for consumption of the *cannabis* product, and allows access to the information in the blocks 602, 604, 606, 610, 612, and optionally 608. Block 616 contains information about the offer for sale and sale of the *cannabis* product as a consumer consumption product, and allows access to the information in the blocks 602, 604, 606, 610, 612, and optionally 608. Block 618 contains information about the use or administration of the *cannabis* product by a healthcare professional, such as dose and dosage of the *cannabis* product provided to a patient. Block 618 allows access to the information in the blocks 602, 604, 606, 610, 612, 620, and optionally 608. Block 620 is also linked to block 618, and contains information about the patient to whom the *cannabis* product is administered, such as presenting symptoms, diagnosis, and other personal health information. Block 618 is linked to block 622. Block 622 contains treatment outcome information about the patient to whom the *cannabis* product is administered and allows access to the information in the blocks 602, 604, 606, 610, 612, 618, 620, and optionally 608.

In an example embodiment, the disclosure provides a method of managing information related to a *cannabis* product across a distributed validated system. The method includes enabling a first authorized user to create a first plurality of data containing genetic profile of a seed used for production of a *cannabis* product. The method includes associating the first plurality of data to a first record which is identified by a first unique identifier. The method includes storing the first record into a memory for access by one or more of a plurality of authorized users using the first unique identifier. The method includes enabling a second authorized user to create a second plurality of data containing plant growth conditions of a crop used for production of the *cannabis* product. The method includes associating the second plurality of data to a second record which is identified by a second unique identifier. The method includes storing the second record into the memory for access by the one or more of the plurality of authorized users using the second unique identifier, wherein the second unique identifier provides access to the first plurality of data and the second plurality of data. The method includes enabling a third authorized user to create a third plurality of data containing manufacturing information for production of the *cannabis* product. The method includes associating the third plurality of data to a third record which is identified by a third unique identifier. The method includes storing the third record into the memory for access by the one or more of the plurality of authorized users using the third unique identifier, wherein the third unique identifier provides access to the first plurality of data, the second plurality of data, and the third plurality of data. The method includes analyzing the *cannabis* product to determine quality and quantity of desired components and undesired components in the *cannabis* product using one or more of: cannabinoid profiling, microbiological testing, analytical testing, food testing, acidified food testing, liquid testing, pathogen testing, quality control testing, and quality assurance testing. The method includes determining concentration of one or more cannabinoids in the *cannabis* product. The method includes enabling a fourth authorized user to create a fourth plurality of data containing measurements of the quality and quantity of desired components and undesired components in the *cannabis* product. The method includes associating the fourth plurality of data to a fourth record which is identified by a fourth unique identifier. The method includes storing the fourth record into the memory for access by the one or more of the plurality of authorized users using the fourth unique identifier, wherein the fourth unique identifier provides access to the first plurality of data, the second plurality of data, the third plurality of data, and the fourth plurality of data.

This application is a continuation-in-part application of U.S. patent application Ser. No. 15/470,562, filed on Mar. 27, 2017, titled "Integrated Systems and Methods of Evaluating *Cannabis* and Cannabinoid Products for Public Safety, Quality Control and Quality Assurance Purposes," which is a continuation application of U.S. patent application Ser. No. 14/312,051, filed on Jun. 23, 2014, now issued as U.S. Pat. No. 9,632,069, titled "Integrated Systems and Methods of Evaluating *Cannabis* and Cannabinoid Products for Public Safety, Quality Control and Quality Assurance Purposes," which claims the benefit of and priority to U.S. Provisional Patent Application No. 61/936,200, filed on Feb. 5, 2014, titled "Systems and Methods of Evaluating *Cannabis* Products for Public Safety, Quality Control and Quality Assurance Purposes"; and U.S. Provisional Patent Application No. 61/939,385, filed on Feb. 13, 2014, titled "Systems and Methods of Evaluating *Cannabis* Products for Public Safety, Quality Control and Quality Assurance Purposes," the disclosures of which are each hereby incorporated by reference in their entireties. This application is also a continuation-in-part application under 35 U.S.C. § 111(a) of the PCT application No. PCT/US2018/42707, filed on Jul. 18, 2018, titled "Compositions Containing Cannabinoid Analog Conjugates and Methods of Use," which claims the benefit of and priority to U.S. Provisional Patent Application No. 62/533,894, filed on Jul. 18, 2017, titled "Compositions Containing Cannabinoid Analog Conjugates and Methods of Use," the disclosures of which are each hereby incorporated by reference in their entireties.

Moreover, the foregoing has broadly outlined certain objectives, features, and technical advantages of the present disclosure and a detailed description of the disclosure so that embodiments of the disclosure may be better understood in light of features and advantages of the disclosure as described herein, which form the subject of certain claims of the disclosure. It should be appreciated that the conception and specific embodiment disclosed may be readily utilized as a basis for modifying or designing other structures for carrying out the same purposes of the present disclosure. It should also be realized that such equivalent constructions do not depart from the disclosure as set forth in the appended claims. The novel features that are believed to be characteristic of the disclosure, both as to its organization and method of operation, together with further objects and advantages is better understood from the following description when considered in connection with the accompanying figures. It is to be expressly understood, however, that such description and figures are provided for the purpose of illustration and description only and are not intended as a definition of the limits of the present disclosure. It will be apparent to those skilled in the art that various modifications and changes can be made within the spirit and scope of the disclosure as described in the foregoing specification.

Further modifications and alternative embodiments of various aspects of the compositions and methods disclosed here will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims.

The foregoing descriptions of methods, compositions, and results obtained using them are provided merely as illustrative examples. Descriptions of the methods are not intended to require or imply that the steps of the various embodiments must be performed in the order presented. As will be appreciated by one of ordinary skill in the art, the steps in the foregoing embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. Various modifications to these embodiments will be readily apparent to those skilled in the art, and the generic principles defined here may be applied to other embodiments without departing from the spirit or scope of the disclosure.

That claimed is:

1. A method of managing information related to a *cannabis* product across a distributed validated system, comprising:

enabling a first authorized user to create a first plurality of data containing genetic profile of a seed used for production of the *cannabis* product;

associating the first plurality of data to a first record which is identified by a first unique identifier;

storing the first record into a memory for access by one or more of a plurality of authorized users using the first unique identifier;

enabling a second authorized user to create a second plurality of data containing plant growth conditions of a crop used for production of the *cannabis* product;

associating the second plurality of data to a second record which is identified by a second unique identifier;

storing the second record into the memory for access by the one or more of the plurality of authorized users using the second unique identifier;

enabling a third authorized user to create a third plurality of data containing manufacturing information for production of the *cannabis* product;

associating the third plurality of data to a third record which is identified by a third unique identifier;

storing the third record into the memory for access by the one or more of the plurality of authorized users using the third unique identifier;

analyzing the *cannabis* product to determine quality and quantity of desired components and undesired components in the *cannabis* product using one or more of: cannabinoid profiling, microbiological testing, analytical testing, food testing, acidified food testing, liquid testing, pathogen testing, quality control testing, and quality assurance testing;

determining concentration of one or more cannabinoids in the *cannabis* product;

enabling a fourth authorized user to create a fourth plurality of data containing measurements of the quality and quantity of desired components and undesired components in the *cannabis* product;

associating the fourth plurality of data to a fourth record which is identified by a fourth unique identifier;

storing the fourth record into the memory for access by the one or more of the plurality of authorized users using the fourth unique identifier;

determining, based on the quality and quantity of the desired components and the undesired components and the concentration of the one or more cannabinoids in the *cannabis* product, whether the *cannabis* product meets regulatory guidelines; and correlating whether the *cannabis* product meets the regulatory guidelines with the first record, the second record, the third record, and the fourth record.

2. The method of claim 1, wherein each of the first identifier, the second identifier, the third identifier, and the fourth identifier provides access to one or more of: the first plurality of data, the second plurality of data, the third plurality of data, and the fourth plurality of data.

3. The method of claim 1, wherein each of the first record, the second record, the third record, and the fourth record includes a timestamp.

4. The method of claim 1, wherein each of the storing the first record step, the storing the second record step, the storing the third record step, and the storing the fourth record step is validated by the one or more of the plurality of authorized users.

5. The method of claim 1, wherein the first plurality of data further includes one selected from the group consisting of: seed purchase request data, grower data, breeder data, seed purchase data, and combinations thereof.

6. The method of claim 1, wherein the second plurality of data includes one selected from the group consisting of: seed planting data, soil data, weather data, water data, moisture data, pressure data, light data, nutrient data, pesticide data, microorganism data, toxicant data, crop growth data, harvesting data, storage data, and combinations thereof.

7. The method of claim 1, wherein the third plurality of data includes one selected from the group consisting of: supply data, distribution data, extraction data, purification data, and combinations thereof.

8. The method of claim 1, further comprising the steps of:

comparing measurements of the quality and quantity of desired components and undesired components in the one or more *cannabis* products and the concentration of one or more cannabinoids against appropriate regulations for consumption of the *cannabis* product; and certifying that the *cannabis* products satisfies or fails the appropriate regulations.

9. The method of claim 1, further comprising the steps of:

enabling a fifth authorized user to create a fifth plurality of data containing dose and dosage of the *cannabis* product provided to a consumer;

associating the fifth plurality of data to a fifth record which is identified by a fifth unique identifier; and storing the fifth record into the memory for access by the one or more of the plurality of authorized users using the fifth unique identifier.

10. The method of claim 9, wherein the fifth identifier provides access to one or more of: the first plurality of data, the second plurality of data, the third plurality of data, the fourth plurality of data, and the fifth plurality of data.

11. The method of claim 9, wherein the fifth record includes a timestamp.

12. The method of claim 9, wherein the fifth plurality of data includes one selected from the group consisting of: physician data, pharmacist data, patient data, consumer data, imaging data, treatment data, treatment outcome data, and combinations thereof.

13. A method of managing information related to a *cannabis* product across a distributed validated system, comprising:

preparing a sample of the *cannabis* product;

testing the sample to determine one or more parameters of: moisture content, microbe/pathogen/mycotoxin profile, pesticide and toxicant profile, residual solvents, heavy metal content, terpene profile, and cannabinoid profile;

enabling an authorized user to create a plurality of data containing parameters obtained in the testing step;

associating the plurality of data to a record which is identified by a unique identifier; and storing the record into a memory for access by one or more of a plurality of authorized users using the unique identifier;

determining, based on the parameters of the *cannabis* product, whether the *cannabis* product meets regulatory guidelines;

correlating whether the *cannabis* product meets the regulatory guidelines with the record.

14. The method of claim 13, further comprising the step of:

storing the *cannabis* product over a predetermined period.

* * * * *